United States Patent
Nakai et al.

(10) Patent No.: US 10,492,742 B2
(45) Date of Patent: Dec. 3, 2019

(54) MEDICAL X-RAY PHOTOGRAPHY APPARATUS FOR PSEUDO INTRAORAL RADIOGRAPHY WITH USER INTERFACE WITH RECTANGULAR FRAME LINES

(71) Applicant: J. MORITA MANUFACTURING CORPORATION, Kyoto-shi, Kyoto (JP)

(72) Inventors: Teruji Nakai, Kyoto (JP); Kouji Yasuda, Kyoto (JP)

(73) Assignee: J. Morita Manufacturing Corporation, Kyoto (JP)

(*) Notice: Subject to any disclaimer, the term of this patent is extended or adjusted under 35 U.S.C. 154(b) by 341 days.

(21) Appl. No.: 14/199,478

(22) Filed: Mar. 6, 2014

(65) Prior Publication Data
US 2014/0254745 A1 Sep. 11, 2014

(30) Foreign Application Priority Data
Mar. 7, 2013 (JP) .................................. 2013-045206

(51) Int. Cl.
| A61B 6/14 | (2006.01) |
| A61B 6/02 | (2006.01) |
| A61B 6/00 | (2006.01) |

(52) U.S. Cl.
CPC ................ *A61B 6/14* (2013.01); *A61B 6/025* (2013.01); *A61B 6/463* (2013.01); *A61B 6/466* (2013.01); *A61B 6/469* (2013.01)

(58) Field of Classification Search
None
See application file for complete search history.

(56) References Cited

U.S. PATENT DOCUMENTS 5,692,027 A * 11/1997 Yoshimura ............... A61B 6/14
                                                        378/116
6,493,415 B1 * 12/2002 Arai ......................... A61B 6/14
                                                        378/38
(Continued)

FOREIGN PATENT DOCUMENTS

| DE | 10 2010 040 096 A1 | 3/2012 |
| JP | H2-234748 | 9/1990 |

(Continued)

OTHER PUBLICATIONS

First Office Action dated Nov. 21, 2016 issued in counterpart EPC Application No. 14000789.9.

*Primary Examiner* — James Choi
(74) *Attorney, Agent, or Firm* — DLA Piper LLP (US)

(57) ABSTRACT

A medical X-ray photography apparatus includes the turning arm and a moving mechanism. The turning arm supports an X-ray generator and an X-ray detector. The moving mechanism includes a turning part that turns the turning arm and a moving part that moves the turning arm along a two-dimensional plane orthogonal to an axial direction of a turning shaft. The medical X-ray photography apparatus also includes a photographic region assignment receiving part that receives an operation to assign a part of a dental arch as a pseudo intraoral radiography region, a main-body control part that controls the moving mechanism based on a movement starting signal to move the turning arm to a predetermined photography starting position corresponding to the pseudo intraoral radiography region, and a signal output switch that includes a movement starting signal output part outputting the movement starting signal to the main body control part.

12 Claims, 22 Drawing Sheets

(56) References Cited

U.S. PATENT DOCUMENTS

| | | | |
|---|---|---|---|
| 2004/0202283 A1* | 10/2004 | Okumura | A61B 6/032 378/145 |
| 2004/0247069 A1 | 12/2004 | Arai et al. | |
| 2009/0168966 A1* | 7/2009 | Suzuki | A61B 6/032 378/116 |
| 2010/0142673 A1 | 6/2010 | Pantsar et al. | |
| 2010/0177865 A1* | 7/2010 | Yoshimura | A61B 6/14 378/19 |
| 2012/0230467 A1* | 9/2012 | Katsumata | A61B 6/032 378/19 |
| 2015/0297158 A1* | 10/2015 | Bothorel | A61B 6/06 378/20 |
| 2015/0305696 A1* | 10/2015 | Yamakawa | A61B 6/14 378/19 |

FOREIGN PATENT DOCUMENTS

| | | |
|---|---|---|
| JP | 2003-245277 A | 9/2003 |
| JP | 2007-29168 A | 2/2007 |
| JP | P2007-136163 A | 6/2007 |
| JP | P2008-114056 A | 5/2008 |
| JP | 2011-152411 A | 8/2011 |
| JP | P2012-217572 A | 11/2012 |
| JP | P2013-536715 A | 9/2013 |
| WO | WO 03/84407 A1 | 10/2003 |
| WO | WO 2009/063974 A1 | 5/2009 |
| WO | WO 2009/133937 A1 | 11/2009 |
| WO | WO 2012/008492 A1 | 1/2012 |

* cited by examiner

F I G. 1 2
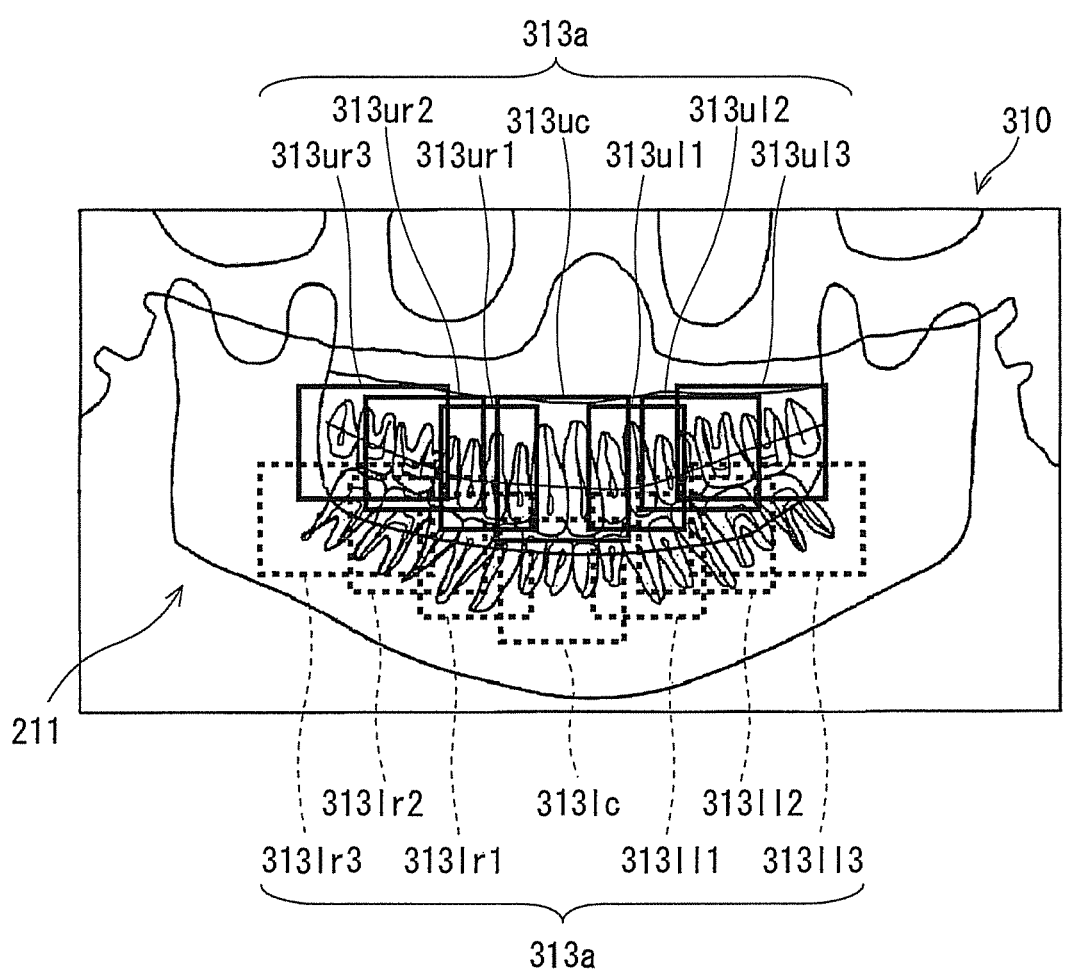

F I G. 1 5
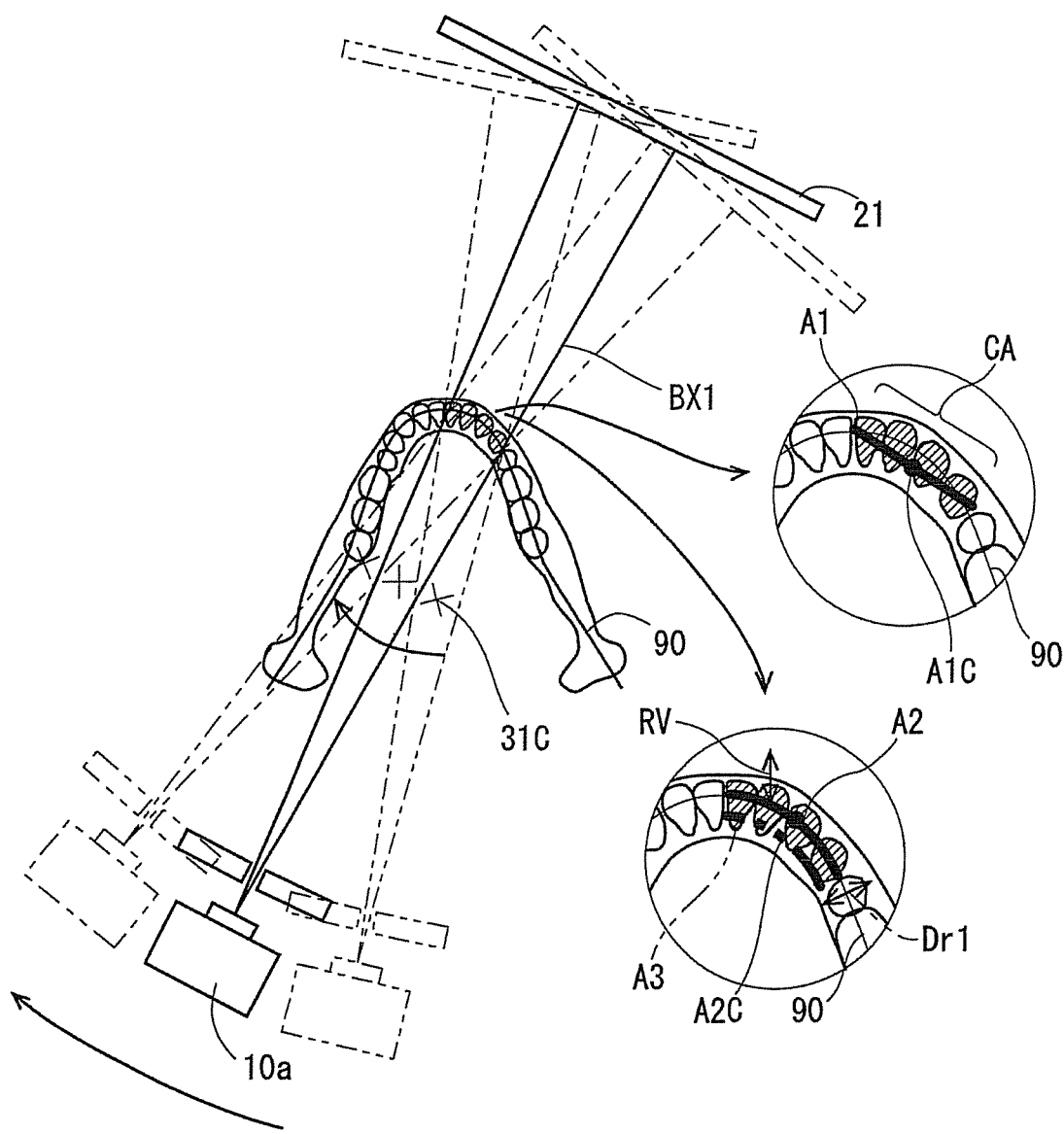

F I G. 1 7
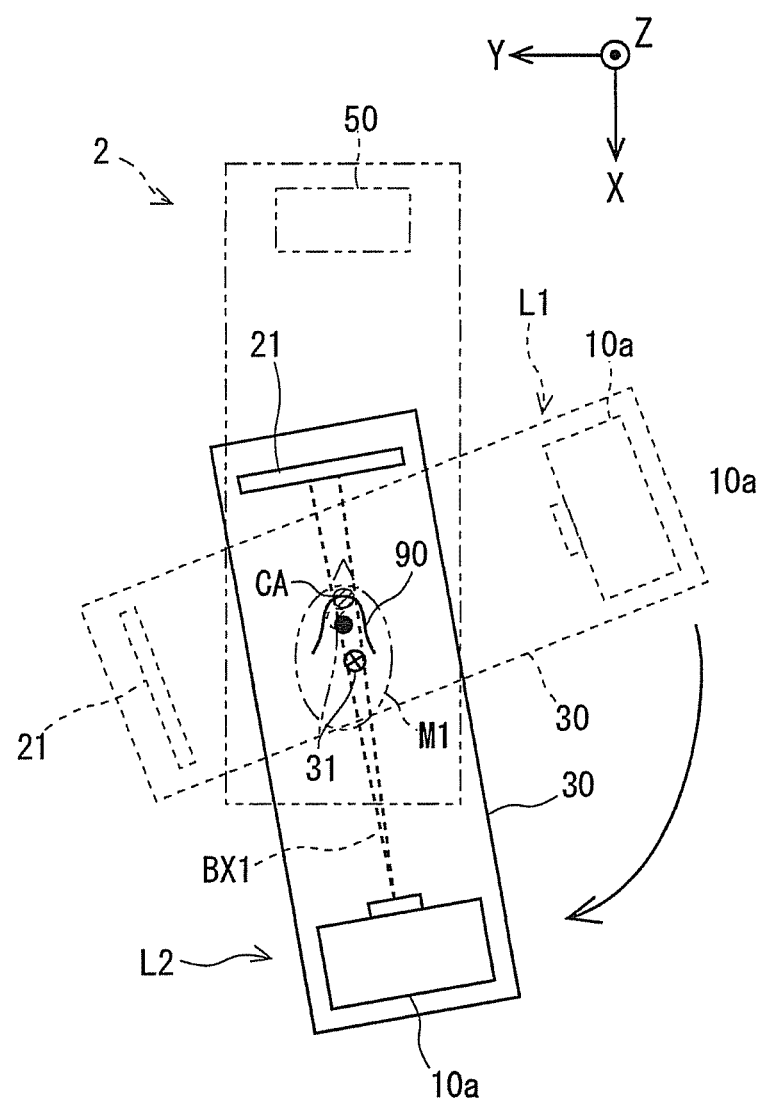

MEDICAL X-RAY PHOTOGRAPHY APPARATUS FOR PSEUDO INTRAORAL RADIOGRAPHY WITH USER INTERFACE WITH RECTANGULAR FRAME LINES

BACKGROUND OF THE INVENTION

Field of the Invention

The present invention relates to a medical X-ray photography apparatus.

Description of the Background Art

There have been proposed some medical X-ray photography apparatuses that perform dental panoramic photography. In this kind of medical X-ray photography apparatus, a support, which supports an X-ray generator and an X-ray detector while the X-ray generator and the X-ray detector are opposed to each other with a subject (a head of a test subject) interposed therebetween, is turned about the subject to perform the panoramic photography (for example, see Japanese Patent Application Laid-Open No. 2011-152411).

What is called intraoral radiography (dental radiography), in which X-ray detection means (such as an X-ray film and an X-ray sensor panel) is disposed in a mouth cavity of a patient to photograph part of a row of teeth or gums, is performed in X-ray photography of a dental field. In the intraoral radiography, because only a local portion is irradiated with an X-ray, advantageously necessity of an X-ray photography apparatus in which a turning arm including the X-ray generator and the X-ray detector at both ends is turned is eliminated, a mechanical configuration is simplified, and the photographing is easily performed. However, unfortunately it is necessary to previously dispose X-ray detection means in a mouth cavity of a patient, and a large burden is placed on the patient. Unless an operator is familiar with relative positioning between the X-ray generator and the X-ray detector, sometimes an image in which X-ray non-irradiation locus called a cone cut is generated is obtained. Sometimes the image in which a size is hardly determined is obtained when an irradiation angle is incorrect.

Therefore, Japanese Patent Application Laid-Open No. 2011-152411 has made a proposal that panoramic photography is performed using a panoramic tomography apparatus and a tomographic image of part of the row of teeth or the gums is acquired using image data obtained by the panoramic photography. The image similar to that obtained by the intraoral radiography can be obtained in a pseudo manner by a tomographic image of part of the row of teeth. In the panoramic photography, the X-ray is detected using an X-ray detector disposed outside a head of the patient. Therefore, the photographing can be performed without having difficulty with the positioning while the burden on the patient is reduced.

In the medical X-ray photography apparatus disclosed in Japanese Patent Application Laid-Open No. 2011-152411, an operation to move the support to a predetermined turning starting position corresponding to a photographic region to start the photographing is performed through an operation part including an operation panel. Therefore, possibly the operation of the operator who starts the X-ray photography is troublesome, and there is room for improvement.

SUMMARY OF THE INVENTION

The present invention is directed to a medical X-ray photography apparatus.

In accordance with a first aspect of the present invention, a medical X-ray photography apparatus includes: a support that support an X-ray generator and an X-ray detector while the X-ray generator and the X-ray detector are opposed to each other with a subject interposed therebetween, the X-ray generator emitting an X-ray beam, the X-ray detector outputting an electric signal according to an intensity of a detected X-ray; a moving mechanism that includes a turning part and a moving part, the turning part turning the support about a turning shaft, the moving part moving the support along a two-dimensional plane orthogonal to an axial direction of the turning shaft; an image processor that generates an X-ray image by processing X-ray image data detected by the X-ray detector, a photographic region assignment receiving part that receives an operation to assign a part of a dental arch as a pseudo intraoral radiography region; a control part that controls the moving mechanism based on a movement starting signal to move the support to a predetermined photography starting position corresponding to the pseudo intraoral radiography region set by the photographic region assignment receiving part; and a signal output switch that includes a movement starting signal output part outputting the movement starting signal to the control part.

According to the first aspect, the support can easily be moved to the default position corresponding to the photographic region by the switch operation. Therefore, a photography starting instruction can easily be issued.

In accordance with a second aspect of the present invention, in the medical X-ray photography apparatus of the first aspect, the signal output switch includes a photography starting signal output part that outputs a photography starting signal to the control part based on reception of a predetermined operation, and, when receiving the photography starting signal, the control part starts the turning of the support moved to the photography starting position, turns the support to a photography ending position corresponding to the pseudo radiography region, and starts irradiation of the subject with the X-ray beam.

According to the second aspect, the operator can start the X-ray irradiation in intended timing. Therefore, the X-ray photography can safely be performed.

In accordance with a third aspect of the present invention, in the medical X-ray photography apparatus of the first aspect, the control part receives the movement starting signal by reception of a predetermined operation, moves the support to the photography starting position, turns the support to a photography ending position corresponding to the pseudo intraoral radiography region, and starts irradiation of the subject with the X-ray beam.

According to the third aspect, the movement of the support to the photography starting position, the turning of the support, and the X-ray irradiation are started only by performing the operation to output the movement starting signal. Therefore, the operation work of the operator can be simplified during the X-ray photography.

In accordance with a fourth aspect of the present invention, in the medical X-ray photography apparatus of any of the first to third aspects, based on a panoramic illustration of a whole jaw or a previously-photographed panoramic X-ray photography image, the photographic region assignment receiving part displays a template including a plurality of rectangular frame lines while superimposing the template on the illustration or the previously-photographed panoramic X-ray photography image, and the photographic region assignment receiving part receives selection assignment as a signal from a photography locus selector that selects any locus from the template.

According to the fourth aspect, which locus is to be photographed can be assigned using the photography locus selector that selects any locus from the template including the plurality of rectangular frame lines. Therefore, the photography locus corresponding to the interesting region can easily be selected.

In accordance with a fifth aspect of the present invention, the medical X-ray photography apparatus of the fourth aspect further includes a multiple-photographing method selector that receives selection of a specific photographing method from a plurality of different multiple-photographing methods. In the medical X-ray photography apparatus, the photographic region assignment receiving part displays the template corresponding to the photographing method selected by the multiple-photographing method selector while arranging the template on the illustration or the previously-photographed panoramic X-ray photography image.

According to the fifth aspect, the multiple-photographing method selector is provided, the specific photographing method can be selected from the plurality of different multiple-photographing methods, and the template is disposed according to the selected photographing method. Therefore, the photography locus satisfying both the multiple-photographing method and the interesting region can be selected according to the size of the interesting region.

In accordance with a sixth aspect of the present invention, in the medical X-ray photography apparatus of the fourth or fifth aspect, the photography locus selector or the multiple-photographing method selector is constructed by an operation display part that is of a touch panel.

According to the sixth aspect, the photography locus selector or the multiple-photographing method selector is easily operated because the display screen provided in the operation display part can be operated as the touch panel.

In accordance with a seventh aspect of the present invention, in the medical X-ray photography apparatus of the fourth or sixth aspect, a change in size of the template is possible by an operation using an operation part, and when the size of the template is changed, the photography starting position is adjusted while an X-ray opening of a beam shaping mechanism of an X-ray generation part is changed according to the change in size of the template.

According to the seventh aspect, the change in size of the template is possible by the operation through the operation part, and, when the size of the template is changed, the X-ray photography starting position is adjusted while the X-ray opening of the beam shaping mechanism of the X-ray generation part is changed according to the change in size of the template. Therefore, X-ray photography starting position can be adjusted according to the interesting region having any size, and the operation or the control can markedly be simplified.

In accordance with an eighth aspect of the present invention, in the medical X-ray photography apparatus of the seventh aspect, proximity of the X-ray detector to the subject is adjusted according to the change in size of the template.

According to the eighth aspect, the proximity of the X-ray detector to the subject can be adjusted according to the change in size of the template, so that a scaling factor can be changed according to the interesting region or the even scaling factor can be obtained.

In accordance with a ninth aspect of the present invention, in the medical X-ray photography apparatus of any of the second to eighth aspects, the signal output switch constitutes a deadman switch, and the control part irradiates the subject with the X-ray beam only when the signal output switch is in an operated state.

According to the ninth aspect, the subject is irradiated with the X-ray beam only when the operator intends to irradiate the subject with the X-ray beam, so that the X-ray photography can more safely be performed.

In accordance with a tenth aspect of the present invention, in the medical X-ray photography apparatus of any of the second to ninth aspects, the signal output switch includes a return signal output part that outputs a return signal to the control part based on reception of a predetermined operation, and when receiving the return signal, the control part returns the support, which is located at the photography ending position, to a default initial position.

The support can be returned to the default initial position in the intended timing of the operator. Therefore, the X-ray generator or the X-ray detector can be returned, after the subject exits the medical X-my photography apparatus, or when the photographing is performed again.

In accordance with an eleventh aspect of the present invention, in the medical X-ray photography apparatus of any of the second to tenth aspects, a first turning speed at which the moving mechanism moves the support to the photography starting position is faster than a second turning speed at which the moving mechanism turns the support from the photography starting position to the photography ending position.

According to the eleventh aspect, the X-ray photography can efficiently be performed by turning the support at a relatively high speed when the X-ray photography is not performed.

In accordance with a twelfth aspect of the present invention, the medical X-ray photography apparatus of any of the first to eleventh aspects further includes an image processor that generates a tomographic image related to a specific tomographic plane from a projection image of the X-ray based on the electric signal output from the X-ray detector. In the medical X-ray photography apparatus, the image processor processes the projection image by different image processing methods, and generates a plurality of tomographic images in which information content related to X-ray absorption of the portion before and behind the specific tomographic plane are different from each other.

According to the twelfth aspect, the tomographic image can be generated according to the diagnostic purpose. Therefore, the diagnostic imaging can effectively be performed.

In accordance with a thirteenth aspect of the present invention, in the medical X-ray photography apparatus of any of the first to twelfth aspects, the medical X-ray photography apparatus is constructed by the support, a main body including the X-ray generator and the X-ray detector, and an information processing device that performs various pieces of information processing, and an operation part that receives an operation of the medical X-ray photography apparatus is provided at least one of the main body and the information processing device.

According to the thirteenth aspect, the medical X-ray photography apparatus can be operated in one of the main body and the information processing device.

In accordance with a fourteenth aspect of the present invention, in the medical X-ray photography apparatus of any of the first to thirteenth aspects, the photographic region assignment receiving part receives the assignment of at least one of a length along the dental arch and a vertical height orthogonal to the dental arch with respect to the pseudo intraoral radiography region based on a predetermined operation.

According to the fourteenth aspect, the photographic region can arbitrarily be set according to the dental arch.

In accordance with a fifteenth aspect of the present invention, in the medical X-ray photography apparatus of any of the ninth to fourteenth aspects, the photographic region assignment receiving part receives the assignment of a tomographic thickness in a buccal-lingual direction orthogonal to the dental arch with respect to the pseudo intraoral radiography region based on the predetermined operation.

According to the fifteenth aspect, the tomographic thickness in the buccal-lingual direction can be assigned, whereby the tomographic image suitable for the diagnostic purpose can be obtained.

In accordance with a sixteenth aspect of the present invention, the medical X-ray photography apparatus of any of the first to fifteenth aspects further includes a photographing condition storage part that stores a photographing condition corresponding to the pseudo intraoral radiography region set by the photographic region assignment receiving part. In the medical X-ray photography apparatus, the control part controls the moving mechanism based on the photographing condition corresponding to the pseudo intraoral radiography region set by the photographic region assignment receiving part.

According to the sixteenth aspect, the pseudo intraoral radiography can be performed according to the photographing condition corresponding to the pseudo intraoral radiography region.

In accordance with a seventeenth aspect of the present invention, in the medical X-ray photography apparatus of any of the first to sixteenth aspects, the control part controls the moving mechanism to enable the X-ray generator and the X-ray detector to perform panoramic photography of the dental arch with respect to panoramic photography region intended for at least one of a whole region of an upper jaw and a whole region of a lower jaw.

According to the seventeenth aspect, the panoramic photography can be performed to one of the whole region of the upper jaw and the whole region of the lower jaw.

In accordance with an eighteenth aspect of the present invention, in the medical X-ray photography apparatus of any of the first to seventeenth aspects, the photographic region assignment receiving part is configured to further receive an operation to assign a part of the dental arch as a target of a CT photography region, and the control part controls the moving mechanism to enable CT photography to be performed with respect to the CT photography region assigned by the photography region assignment receiving part.

According to the eighteenth aspect, the CT photography can be performed in the medical X-ray photography apparatus.

In accordance with a nineteenth aspect of the present invention, the medical X-ray photography apparatus of any of the first to eighteenth aspects further includes a cephalic part that performs cephalic photography.

According to the nineteenth aspect, the cephalic photography can be performed in the medical X-ray photography apparatus.

Thus, an object of the present invention is to provide a technology for moving the support to the turning start position corresponding to the photographic region to simplify the photography starting operation.

These and other objects, features, aspects and advantages of the present invention will become more apparent from the following detailed description of the present invention when taken in conjunction with the accompanying drawings.

BRIEF DESCRIPTION OF THE DRAWING

FIGS. 11A to 14 are views illustrating other examples of an image display portion;

FIG. 15 is a schematic plan view illustrating a situation of the pseudo intraoral radiography when viewed in a −Z-direction from a +Z-side;

FIG. 17 is a schematic plan view illustrating a second phase of the X-ray photography;

DESCRIPTION OF THE PREFERRED EMBODIMENTS

Hereinafter, a preferred embodiment of the present invention will be described with reference to the accompanying drawings. In the following drawings, for the sake of convenience, sometimes a size or the number of pieces of each part is illustrated while magnified or simplified as needed basis.

1. Preferred Embodiment

Figure 1:
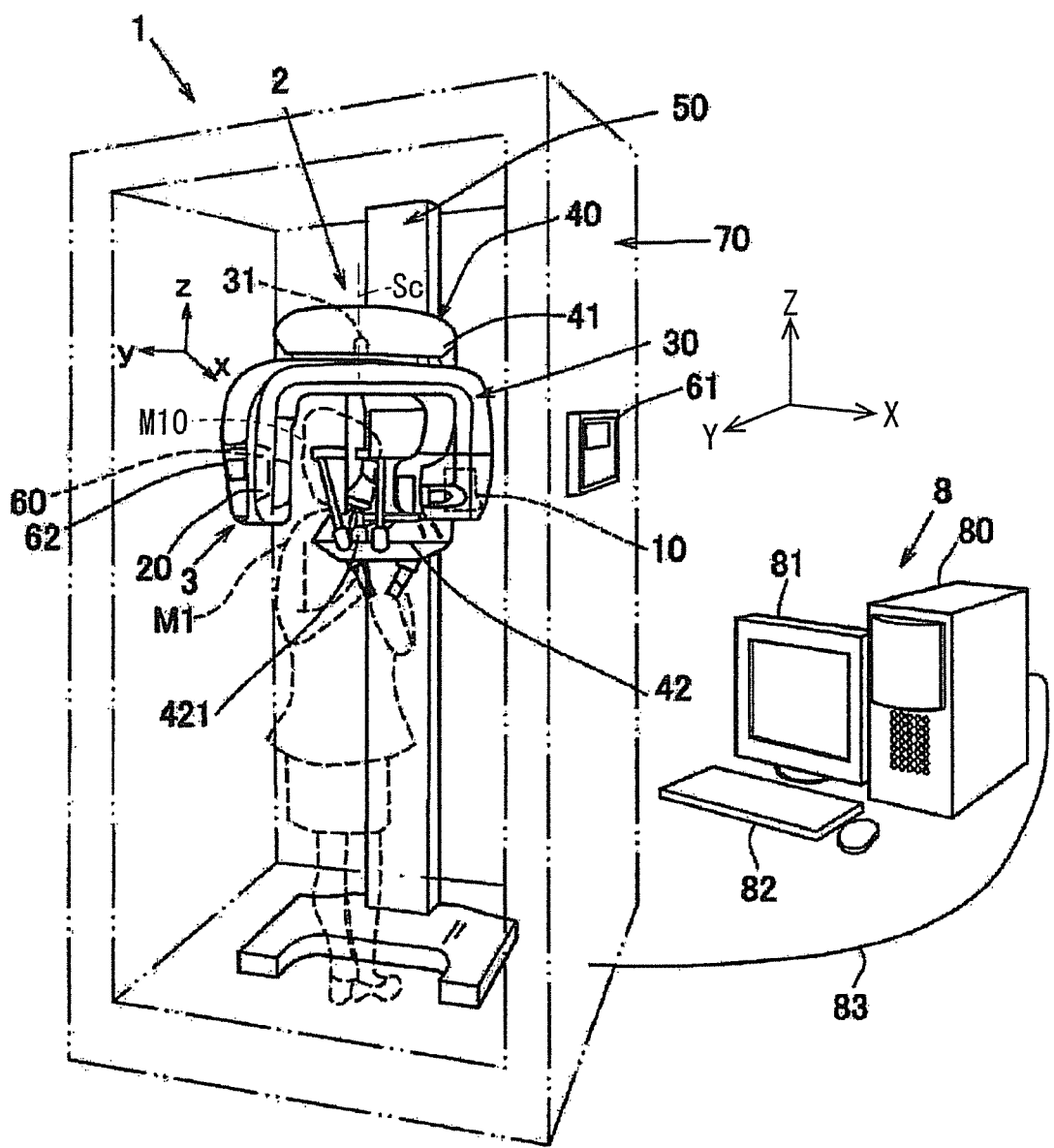
FIG. 1 is a schematic perspective view of a medical X-ray photography apparatus according to a preferred embodiment.
Figure 2:
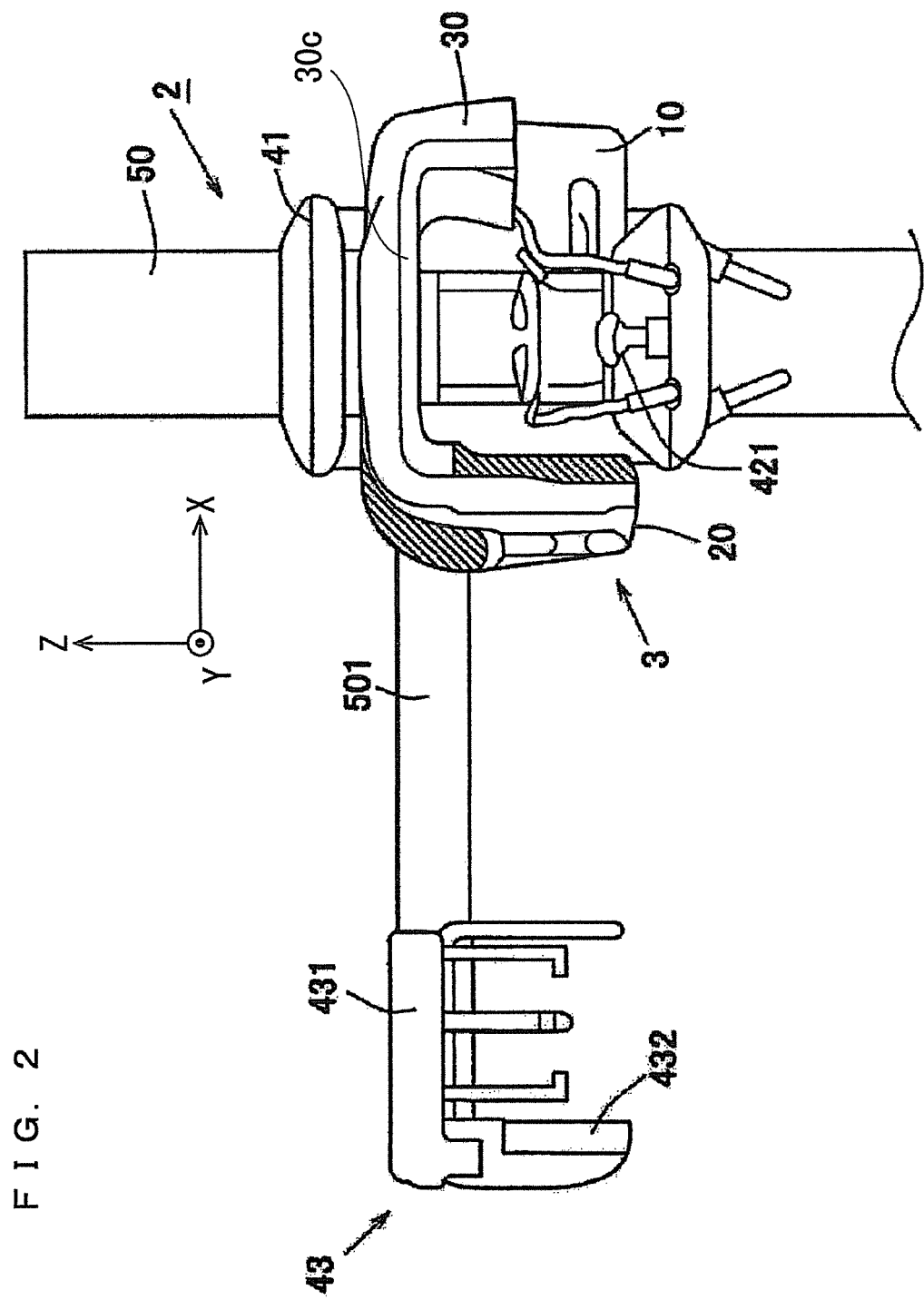
FIG. 2 is a partial front view of the medical X-ray photography apparatus on which a cephalic part is mounted.
Figure 3:
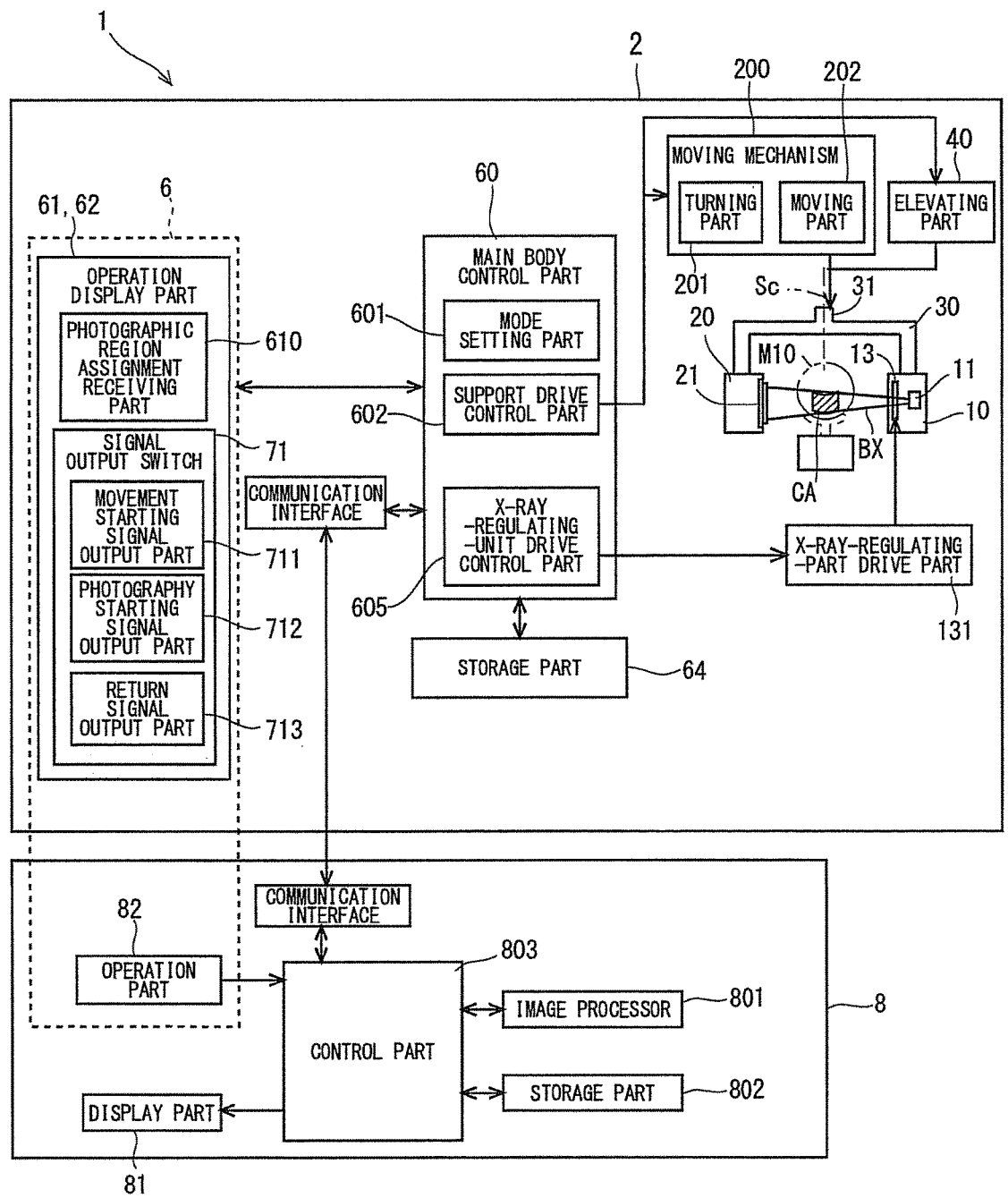
FIG. 3 is a block diagram illustrating a configuration of the medical X-ray photography apparatus.
Figure 4:
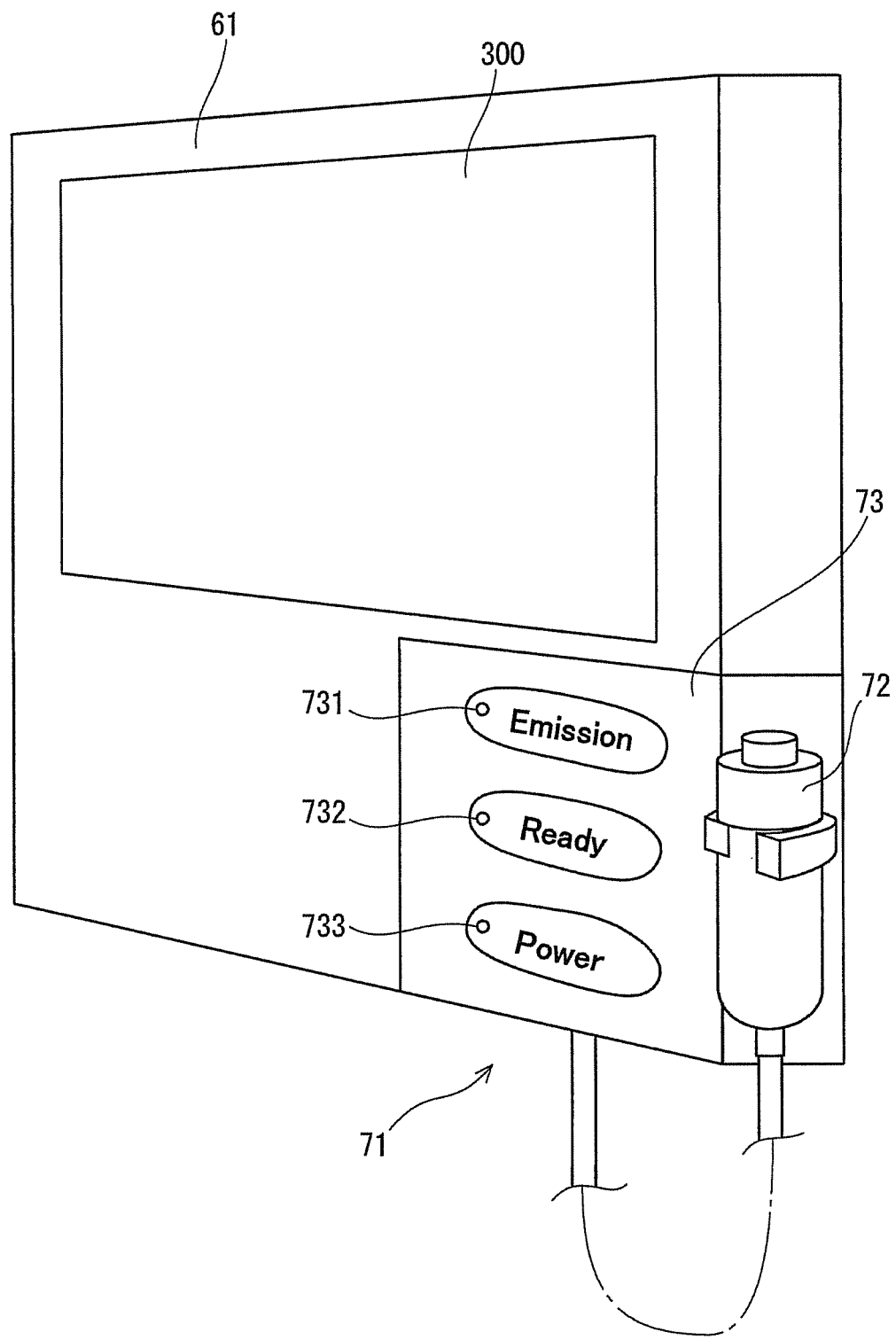
FIG. 4 is a front view of a signal output switch.

A medical X-ray photography apparatus 1 according to a first preferred embodiment will be described below. FIG. 1 is a schematic perspective view of the medical X-ray photography apparatus 1 of the first preferred embodiment. FIG. 2 is a partial front view of the medical X-ray photography apparatus 1 on which a cephalic part 43 is mounted. FIG. 3 is a block diagram illustrating a configuration of the medical X-ray photography apparatus 1. FIG. 4 is a front view of a signal output switch 71.

The medical X-ray photography apparatus 1 is roughly divided into operation display parts 61 and 62, a main body 2, and an information processing device 8. The operation display parts 61 and 62 act as display parts while setting a photographic region CA. The main body 2 collects projection data (frame data) expressing an X-ray projection image by performing X-ray photography to the photographic region CA set by the operation display part 61. The information processing device 8 generates various images by processing the projection data collected by the main body 2.

A main body control part 60 of the main body 2 and a control part 803 and an image processor 801 (see FIG. 3) of the information processing device 8 perform the X-ray photography according to a program IMP of the X-ray photography.

Desirably, in the site of the X-ray photography, the main body 2 is accommodated in a hollow, vertically-long, rectangular X-ray protective chamber 70. The main body 2, the operation display part 61 mounted on a wall surface (an outside portion of a wall) of the X-ray protective chamber 70, and the information processing device 8 disposed outside the X-ray protective chamber 70 are connected to one another through a connection cable 83.

The main body 2 includes an X-ray generation part 10 and an X-ray detection part 20. The X-ray generation part 10 emits an X-ray beam BX (such as an X-ray cone beam and an X-ray slit beam) including a bundle of X-rays toward a subject M1. The X-ray detection part 20 detects the X-ray beam, which is transmitted through the subject M1 after emitted from the X-ray generation part 10. The main body 2 also includes a turning arm 30 serving as the support supporting the X-ray generation part 10 and the X-ray detection part 20, a vertically extending pillar 50, an elevating part 40 that can vertically be elevated with respect to the pillar 50 while suspending the turning arm 30, and a main body control part 60. The X-ray generation part 10, the X-ray detection part 20, and a beam forming mechanism 13 of the X-ray generation part 10 disposed on a side of the X-ray detection part 20 constitute a photographic mechanism 3.

The X-ray generation part 10 and the X-ray detection part 20 are suspended from and fixed to both end portions of a turning part 30c of the turning arm 30, respectively. The X-ray generation part 10 and the X-ray detection part 20 are supported so as to be opposed to each other. The turning arm 30 is suspended from the elevating part 40 with a vertically extending turning shaft 31 interposed therebetween.

The turning arm 30 has a substantially inverted U-shape when viewed from a front side. The turning arm 30 turns about the turning shaft 31 serving as a turning center Sc provided in an upper end portion of the turning part 30c. In the preferred embodiment, the elevating part 40 includes an upper frame 41 that extends frontward from an upper portion of the elevating part 40 when viewed from the front side.

The turning arm 30 of the preferred embodiment is formed into a U-shape. Alternatively, the turning arm 30 may be formed into another shape. For example, an annular member that is rotatably fitted in an outer circumferential portion of a columnar-shaped member fixed above the subject M1 with, for example, a ball bearing interposed therebetween may be used instead of the turning arm. In this case, the X-ray generation part 10 and the X-ray detection part 20 are attached to the annular member so as to be opposed to each other. The annular member rotates along the outer circumferential portion of the columnar-shaped member, which allows the X-ray generation part 10 and the X-ray detection part 20 to rotate about a head M10 of the subject M1 with the head M10 interposed therebetween.

Hereinafter, a direction (in the preferred embodiment, a vertical direction, namely, a longitudinal direction) parallel to an axial direction of the turning shaft 31 is referred to as a "Z-axis direction", a direction intersecting the Z-axis direction is referred to as an "X-axis direction", and a direction intersecting the X-axis direction and the Z-axis direction is referred to as a "Y-axis direction". The X-axis direction and the Y-axis direction may arbitrarily be defined. However, in the preferred embodiment, when a test person serving as the subject M1 is positioned in the medical X-ray photography apparatus 1 to directly face the pillar 50, a side-to-side direction of the test person is defined as the X-axis direction, and a front-back direction of the test person is defined as the Y-axis direction. In the preferred embodiment, it is assumed that the X-axis direction, the Y-axis direction, and the Z-axis direction are orthogonal to one another. Hereinafter, sometimes the Z-axis direction is referred to as the vertical direction, and a direction on a plane defined by a two-dimensional direction of the X-axis direction and Y-axis direction is referred to as a horizontal direction. Sometimes the "Z-axis direction" is referred to as a "Z-direction", the "X-axis direction" is referred to as an "X-direction", and the "Y-axis direction" is referred to as a "Y-direction".

On the other hand, as to three-dimensional coordinates on the turning arm 30, a direction in which the X-ray generation part 10 and the X-ray detection part 20 are opposed to each other is referred to as a "y-axis direction", a horizontal direction orthogonal to the y-axis direction is referred to as an "x-axis direction" and a vertical direction orthogonal to the x-axis direction and y-axis direction is referred to as a "z-axis direction". Hereinafter, sometimes the "z-axis direction" is referred to as a "z-direction", the "x-axis direction" is referred to as an "x-direction", and the "y-axis direction" is referred to as a "y-direction".

In the preferred embodiment and subsequent preferred embodiments, the z-axis direction and the Z-axis direction are parallel to each other. The turning arm 30 of the preferred embodiment turns about the vertically extending turning shaft 31 as a rotational axis (the turning axis). Accordingly, the xyz orthogonal coordinate system rotates about the Z-axis (=the z-axis) with respect to the XYZ orthogonal coordinate system.

In the preferred embodiment, as illustrated in FIG. 1, when the test person directly faces the pillar 50, a right-hand direction is referred to as a (+X)-direction, a back-side direction is referred to as a (+Y)-direction, and an upwardly vertical direction is referred to as a (+Z)-direction. When the X-ray generation part 10 and the X-ray detection part 20 are viewed from above in plan, the direction from the X-ray generation part 10 toward the X-ray detection part 20 is referred to as a +y-direction, a left-hand direction from a −y-side toward the +y-direction is referred to as a +x-direction, and an upwardly vertical direction is referred to as a +z-direction.

The elevating part 40 includes the upper frame 41 (a first support retention part) and a lower frame 42, and engages the vertically-standing pillar 50. The turning shaft 31 is attached to the upper frame 41 that acts as a retention part for the turning arm 30. The elevating part 40 moves vertically along the pillar 50, whereby the turning arm 30 serving as the support moves up and down.

As to a structure that turns the turning arm 30, the turning arm 30 may be provided so as to be turnable with respect to the turning shaft 31 attached to the upper frame 41 so as to be non-turnable, and the turning arm 30 may turn with respect to the turning shaft 31. Alternatively, the turning arm 30 may be fixed so as to be non-turnable with respect to the turning shaft 31 provided to the upper frame 41 so as to be turnable, and the turning arm 30 may turn by turning the turning shaft 31.

In the former, a torque of a turning motor (a support turning drive part) can act on the turning arm 30 through a power transmission mechanism such as a belt and a pulley. For example, the turning motor is fixed to the inside of the turning arm 30, and an annular belt is entrained about both the pulley fixed to the rotational shaft of the turning motor and the turning shaft 31 such that the torque of the turning motor acts on the turning arm 30. In this case, a bearing member such as a bearing may be interposed between the turning shaft 31 and the turning arm 30.

Alternatively, a turning motor that turns the turning arm 30 about the turning shaft 31 may be provided in the upper frame 41, and the transmission mechanism, which includes a belt, a pulley, and a rotational shaft and passes through the turning shaft 31, may transmit the torque of the turning motor to the turning arm 30 to turn the turning arm 30.

Like the latter, the turning arm 30 may be unturnably fixed to the turning shaft 31 turnable with respect to the upper frame 41, and the turning arm 30 may turn by turning the turning shaft 31 as a matter of course. In this structure, the turning motor is fixed to the inside of the upper frame 41, and the torque of the turning motor can act on the rotation of the turning shaft 31 using the transmission mechanism such as a roller. In this case, the bearing member such as the bearing may be interposed between the turning shaft 31 and the upper frame 41.

In the preferred embodiment, the turning shaft 31 is configured to extend vertically. Alternatively, it is also conceivable that the turning shaft 31 is obliquely disposed at any angle with respect to the vertical direction.

The bearing is interposed between the turning shaft 31 and the turning arm 30. Therefore, the turning arm 30 can rotate smoothly with respect to the turning shaft 31. The turning shaft 31, the transmission mechanism including the bearing, the belt, the pulley, and the rotational shaft, and the turning motor are an example of a turning part 201 (see FIG. 3) that turns the turning arm 30. In FIG. 3, the turning shaft 31 exists outside the turning part 201. This is because FIG. 3 illustrates the fact that the turning shaft 31 is connected to the turning arm 30. That is, the turning part 201 relatively turns the turning arm 30 (the support) about the turning shaft 31 with respect to the head M10 of the subject M1 (the test person). Therefore, the turning part 201 relatively turns an X-ray generator 10a and an X-ray detector 21 about the head M10 of the subject M1. It is considered that the subject includes a portion corresponding to the photographic region, an individual (the test person in the above case) including the photographic region, and part (the head in the above case) of the photographic region of the individual.

The X-ray detector 21 is constructed by a plurality of planarly-arrayed X-ray sensors each of which outputs an electric signal according to an intensity of the detected X-ray. In the preferred embodiment, a generally-used CCD sensor is used in the panoramic photography. For example, TDI (Time Delay Integration) is used to read a charge from the CCD. Any electrically imaging sensor may be used as the X-ray sensor as long as a frame image is obtained, and a MOS sensor and a CMOS sensor are also suitably used as the X-ray sensor. Another solid-state imaging element including a TFT may be used. An image intensifier (I.I.) may be used.

In the preferred embodiment, the turning arm 30 turns with respect to the turning shaft 31 that does not rotate with respect to the upper frame 41. However, as described above, it is also conceivable that the turning shaft 31 fixed to the turning arm 30 is turned with respect to upper frame 41 to turn the turning arm 30. In this case, the bearing that rotatably supports the turning shaft 31 is formed in the upper frame 41.

The main body 2 includes a moving part 202 that relatively moves the turning arm 30 in the direction (the X-direction, the Y-direction, or the direction having components of the X-direction and the Y-direction) perpendicular to the turning shaft with respect to the head M10 of the subject M1. The moving part 202 can be constructed by an XY table, which is fixed onto the upper frame 41 or the turning arm 30. The XY table includes a table member that moves in the X-axis direction, a table member that moves in the Y-axis direction, and a motor that moves the table members in the X-axis direction and the Y-axis direction. In the case that the XY table is fixed to the upper frame 41, the XY table is fixed to the upper end portion of the turning shaft 31. In this case, by driving the XY table, the turning arm 30 moves in the direction perpendicular to the turning shaft 31 together with the turning shaft 31. In the case that the XY table is fixed onto the turning arm 30, the XY table is fixed to the lower end portion of the turning shaft 31. In this case, only the turning arm 30 moves in the direction perpendicular to the turning shaft 31.

Using the XY table, the turning center of the X-ray generator 10a and the X-ray detector 21 can be fixed to a place different from the turning shaft 31 serving as the mechanical turning axis. Hereinafter, this control is referred to as a turning center setting by turning shaft moving control.

For example, in CT photography, a center of the photographic region CA is set onto a line connecting centers of the X-ray generator 10a and the X-ray detector 21 when the X-ray generator 10a, the X-ray detector 21, and the photographic region CA are looked down in the Z-direction. The axis center of the turning shaft 31 is set to a place different from the photographic region CA on the line connecting the centers of the X-ray generator 10a and the X-ray detector 21. Under this geometric condition, the turning arm 30 is turned about the turning shaft 31, and the XY table turns the turning shaft 31 about the center of the photographic region CA by an angle equal to a turning angle of the turning arm 30. Thus, the CT photography can also be performed by irradiating the photographic region CA with the X-ray cone beam while the X-ray generator 10a and the X-ray detector 21 turn about the center of the photographic region CA.

Japanese Patent Application Laid-Open No. 2007-29168 and International Patent Publication No. 2009/063974, which have been filed by the applicant of the present application, disclose the configuration implementing the above CT photography, and the configuration can also be appropriately applied to the present application.

In the preferred embodiment, a moving mechanism 200 including the turning part 201 and the moving part 202 can relatively move the turning arm 30 with respect to the head M10 of the subject M1. However, the moving mechanism is not limited to the above configuration. For example, the main body 2 may be configured such that the moving mechanism rotates the subject M1 about a predetermined rotational axis, or such that the moving mechanism moves the subject M1 in the direction perpendicular to the rotational axis. A seat on which the subject M1 sits may be provided to fix the subject M1 in a seated posture. For example, in the case that the X-ray photography is performed while the subject M1 is moved, blurring of the subject M1 can be reduced by moving the subject M1 in the seated posture.

A subject retention part 421 is provided in the lower frame 42. The subject retention part 421 includes a head holder that fixes the head M10 of the subject M1 of a human body from the right and left sides and a chin rest that fixes a chin.

The turning arm 30 is disposed at a proper position by elevating the elevating part 40 according to a body height of the subject M1. At this point, the subject M1 is fixed to the subject retention part 421. In the example illustrated in FIG. 1, the subject retention part 421 retains the subject M1 such that a body axis of the subject M1 is substantially aligned with the axial direction of the turning shaft 31. As used herein, the "body axis" means a symmetrical axis, which is set in the case that the human body is considered to be substantially symmetrical when viewed from the front side.

A support drive control part 602 (see FIG. 3) of the main body control part 60 controls operations of the elevating part 40 and the moving mechanism 200.

The main body control part 60 is a control part that controls the operation of each part of the main body 2. For example, the main body control part 60 acts as an X-ray regulating control part and a drive control part. As illustrated in FIG. 1, the main body control part 60 is disposed inside the X-ray detection part 20.

A operation display part 62 is attached to the outside of the main body control part 60, namely, on the +y side of the X-ray detection part 20. The operation display part 62 includes buttons that are used to input various designations or a touch panel that displays various pieces of information.

The operation display part 61 is attached to the outside of the wall of the X-ray protective chamber 70 that accommodates the main body 2 therein. The operation display part 61 is connected to the main body control part 60, and includes buttons that are used to input various designations and a touch panel that displays various pieces of information. The operation display part 61 and the operation display part 62 are included in the operation part 6 of the medical X-ray photography apparatus 1, because the operation display part 61 and the operation display part 62 include the function as the operation part in addition to the function as the display part. The operation part 82 of the information processing device 8 is also included in the operation part 6.

The operation display part 61 and the operation display part 62 are an example of the operation part on the main body side, and the operation part 82 is an example of the operation part on the information processing device side. In the operation part on the main body side, the operation display part 61 is an example of the operation part outside the X-ray protective chamber.

An operator (for example, a practitioner) may operate the main body 2 using the operation display part 62, or operate the main body 2 using the operation display part 61. The operation display part 62 may differ from the operation display part 61 in an operation content or a display content. Part or whole of the operation content or display content may be common to the operation display part 62 and the operation display part 61.

One of the operation display part 62 and the operation display part 61 may be eliminated. In the case that the X-ray protective chamber 70 is eliminated, the operation display part 61 may be eliminated. Although the display and operation performed by the operation display part 61 are described below, the display and operation performed by the operation display part 61 may be replaced with the display and operation performed by the operation display part 62.

The operation display part 61 is also used, for example, to designate the position of the photographic region of a biological organ. There are various modes in the X-ray photography, and the mode may be selected through the operation of the operation display part 61.

The operation display part 61 includes a signal output switch 71. FIG. 4 is a view illustrating the signal output switch 71 that partially constitutes the operation display part 61 provided on the wall surface of the X-ray protective chamber. The signal output switch 71 includes an operation switch 72 that is operated by the operator and an LED display part 73. The LED display part 73 includes an emission LED 731 that is lit while the X-ray generator 10a emits the X-ray, a readiness LED 732 that is lit when the turning arm 30 moves to a predetermined photography starting position to be ready for the X-ray photography, and a main power LED 733 that is lit when a power switch of the main body 2 is in an on state.

The signal output switch 71 includes a movement starting signal output part 711 that outputs a movement starting signal to the main body control part 60, a photography starting signal output part 712 that outputs a photography starting signal to the main body control part 60, and a return signal output part 713 that outputs a return signal to the main body control part 60, thereby acting as the movement starting signal output part, the photography starting signal output part, and the return signal output part.

When the movement starting signal is output to the main body control part 60, the main body control part 60 controls the moving mechanism 200 to move the turning arm 30, and arranges the X-ray generator 10a in a photography starting position where the turning is started in order to irradiate a photography target region with the X-ray beam. The movement of the turning arm 30 includes the turning about the turning shaft 31 and the horizontal movement.

When the photography starting signal is output to the main body control part 60, the main body control part 60 starts the X-ray photography. Specifically, the main body control part 60 controls the moving mechanism 200 to move the turning arm 30 to a photography ending position from the photography starting position according to the set photographic region. In association with the movement, the main body control part 60 controls the X-ray generation part 10 to irradiate the subject M1 with the X-ray beam. The X-ray detector 21 detects the X-ray beam during the X-ray photography, whereby an X-ray projection image to which the subject M1 is projected is collected as X-ray projection image data, for example, in the form of frame data, and the X-ray projection image data is stored in a storage part 64 or a storage part 802 of the information processing device 8. When moving the turning arm 30 to the photography ending position, the main body control part 60 receives a photography ending signal from a detector that detects that the turning arm 30 arrives at the photography ending position, and stops the irradiation of the X-ray beam.

A microswitch that detects contact of a member may be used as the detector that detects that the turning arm 30 arrives at the photography ending position, or an optical detector may monitor the movement of the turning arm 30. Alternatively, in the case that the moving mechanism 200 is constructed by a pulse motor, a determination that the turning arm 30 arrives at the photography ending position is made to transmit the photography ending signal when the predetermined number of pulses is detected using a pulse counter.

A current or a voltage, which is supplied to the X-ray tube of the X-ray generator 10*a*, may be turned on and off to start or end the X-ray emission, thereby turning on and off the irradiation of the X-ray beam. Alternatively, the irradiation of the X-ray beam may be turned on and off by passage or cut-off of the X-ray beam, which is emitted from the X-ray generator 10*a*, using a later-described X-ray regulating part.

After predetermined time elapses since the turning arm 30 moves to the photography ending position, the turning arm 30 moves to a predetermined retractable position such that the subject M1 can exit the main body 2 of the medical X-ray photography apparatus 1. When the turning arm 30 moves to the retractable position, the subject M1 can exit the main body 2 without obstruction of the X-ray generation part 10 or the X-ray detection part 20.

The photography starting position and photography ending position of the turning arm 30 and the on and off positions of the X-ray irradiation are previously determined according to the photographic region, and stored in the storage part 64 as a photographing condition. The photographing condition corresponding to the photographic region, which is assigned through the operation display part 61 (or the operation display part 62) that acts as a later-described photographic region assignment receiving part 610, is called from the storage part 64, and the main body control part 60 controls the moving mechanism 200 based on the called photographing condition. The photographing condition may be stored in a storage part 802 of the later-described information processing device 8, and checked on the display part 81 using the operation part 82.

When the return signal is output to the main body control part 60, the main body control part 60 controls the moving mechanism 200 to move the turning arm 30 from the retractable position to the initial position.

In the preferred embodiment, the signal output switch 71 includes only one operation switch 72 as the operation part that can be operated by the operator. The operation of the operation switch 72 outputs the movement starting signal, the photography starting signal, and the return signal to the main body control part 60.

When the operation switch 72 is operated from the initial state, the movement starting signal output part 711 outputs the movement starting signal. When the movement of the turning arm 30 is completed, the readiness LED 732 is lit. Therefore, the photography starting signal output part 712 becomes a state in which the photography starting signal can be output. At this point, when the operation switch 72 is operated, the signal output switch 71 outputs the photography starting signal.

When the photography starting signal is output, the turning arm 30 moves from the photography position to the photography ending position while the X-ray irradiation is performed. When the X-ray irradiation is ended, the return signal output part 713 outputs the return signal, and the turning arm 30 returns from the photography ending position to the initial position. The operation switch 72 is operated while the return signal can be output, thereby outputting the return signal.

The movement starting signal, the photography starting signal, and the return signal may be signals indicating different pieces of information, or signals indicating identical information. In the case that the movement starting signal, the photography starting signal, and the return signal are the signals indicating the identical information, the main body control part 60 may determine the state (such as the pre-X-ray photography state (an initial state), the turning starting state, the state in which preparation of the X-ray irradiation is completed, the state during the X-ray irradiation, and the post-X-ray photography state) of the main body 2 to interpret each signal transmitted from the signal output switch 71.

The signal output switch 71 may be constructed as a deadman switch. In this case, the signal output switch 71 outputs a predetermined signal to the main body control part 60 only when the signal output switch 71 is pressed by the operator (in an operated state). Only when receiving the signal, the main body control part 60 controls the X-ray generation part 10 such that the subject M1 is irradiated with the X-ray beam. Therefore, the subject M1 is irradiated with the X-ray beam only when the operator intentionally presses the signal output switch 71, so that the X-ray photography can safely be performed.

Desirably the signal output switch 71 is provided in the operation display part 61. Alternatively, the signal output switch 71 may be provided near the operation display part 61 while separated from the operation display part 61, or only the signal output switch 71 constituting the operation part 6 may be provided outside the wall surface of the X-ray protective chamber 70 while the operation display part 61 is partially eliminated.

A signal output switch 71*a* that transmits the signal identical to that of the signal output switch 71 may be provided in the information processing device 8. However, in this case, the signal is transmitted from the signal output switch 71*a* to the control part 803 of the information processing device 8, and further transmitted to the main body control part 60, thereby controlling an operation of the main body 2. Alternatively, the signal may be transmitted from the control part 803 to the main body control part 60 while the operation part 82 of the information processing device 8 has the function of transmitting the signal identical to that of the signal output switch 71.

The information processing device 8 includes an information processing main body 80, a display part 81 that is constructed by a display device such as a liquid crystal monitor, and an operation part (the operation part on the information processing device side) 82 that is constructed by a keyboard and a mouse. The operator (the practitioner) can input various designations to the information processing device 8 through the operation part 82. The display part 81 may include the touch panel. In this case, the display part 81 may include part of or whole of the functions of the operation part 82.

All the operations performed by the operation display parts 61 and 62 on the main body side may be configured to be able to be performed by the operation part 82 on the information processing apparatus side, almost all the operations performed by the operation display parts 61 and 62 on the main body side may be configured to be performed by the operation part 82, or all the operations may be configured to be performed by the operation part 82 while the operation display parts 61 and 62 are eliminated.

For example, the information processing main body 80 includes a computer or a workstation. The information processing main body 80 transmits and receives various pieces of data to and from the main body 2 through the connection cable 83 serving as the communication cable. Alternatively, the main body 2 and the information processing main body 80 may wirelessly conduct data communication with each other.

For example, the information processing device 8 processes the projection data acquired by the main body 2, and reconstructs three-dimensional data (volume data) expressed in the voxel form. For example, the information processing device 8 sets a specific cutting plane to the three-dimensional data, and a tomographic image is reconstructed in the specific cutting plane.

It is also considered that the medical X-ray photography apparatus 1 is used as an apparatus that collects only the frame data by the X-ray photography. In such cases, it is considered that the information processing device 8 is eliminated.

As illustrated in FIG. 2, the cephalic unit 43 may be attached to the medical X-ray photography apparatus 1. For example, the cephalic unit 43 is attached to an arm 501 that extends horizontally from the elevating part 40. The cephalic unit 43 includes a fixture 431 that fixes the head M10 to a given position and an X-ray detector 432 for cephalic photography. For example, a cephalic unit disclosed in Japanese Patent Application Laid-Open No. 2003-245277 or a cephalic unit similar thereto can be used as the cephalic unit 43.

<X-Ray Regulating Part>

Figure 5:
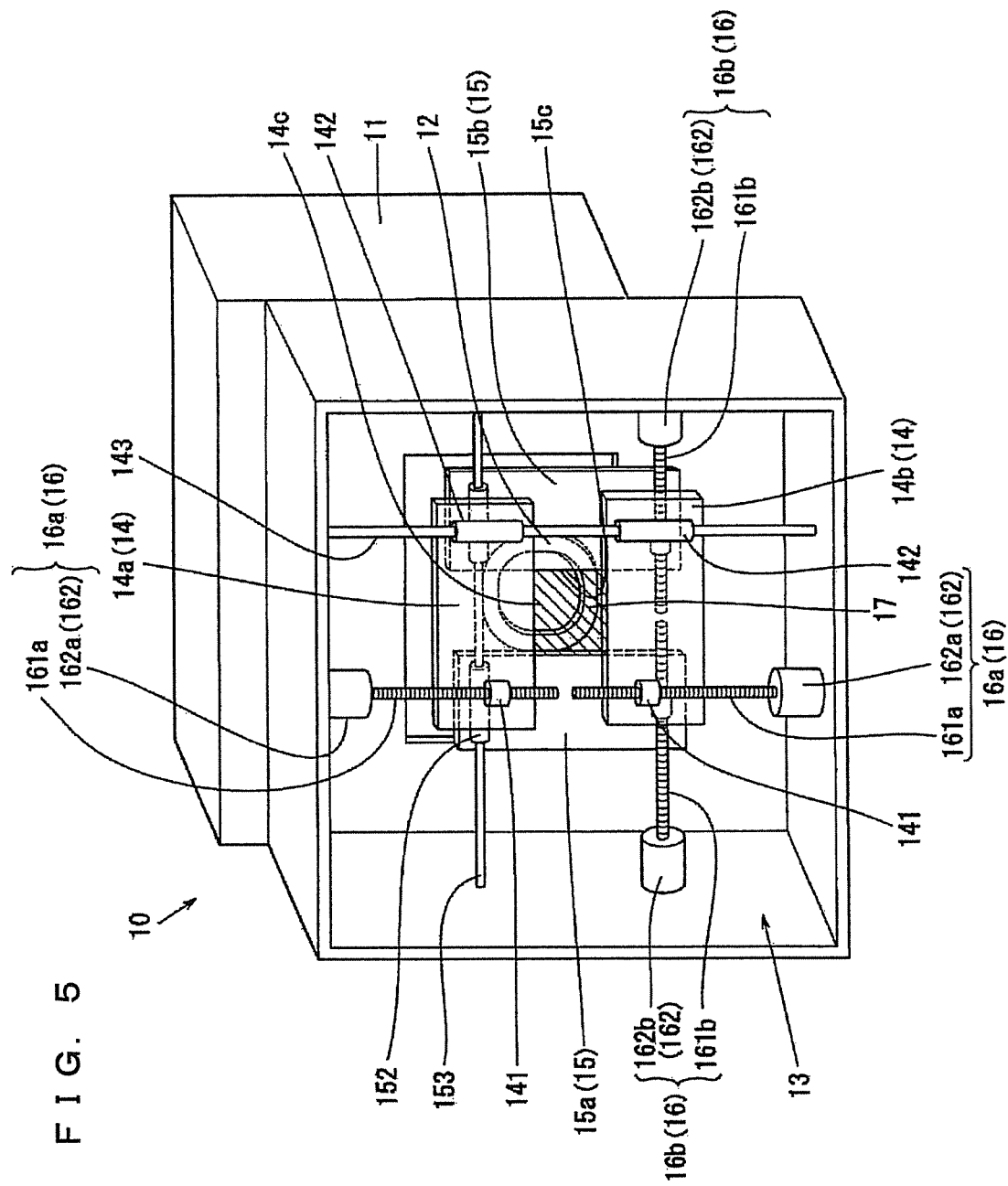
FIG. 5 is a schematic perspective view of a beam forming mechanism (an X-ray regulating part)
Figure 6:
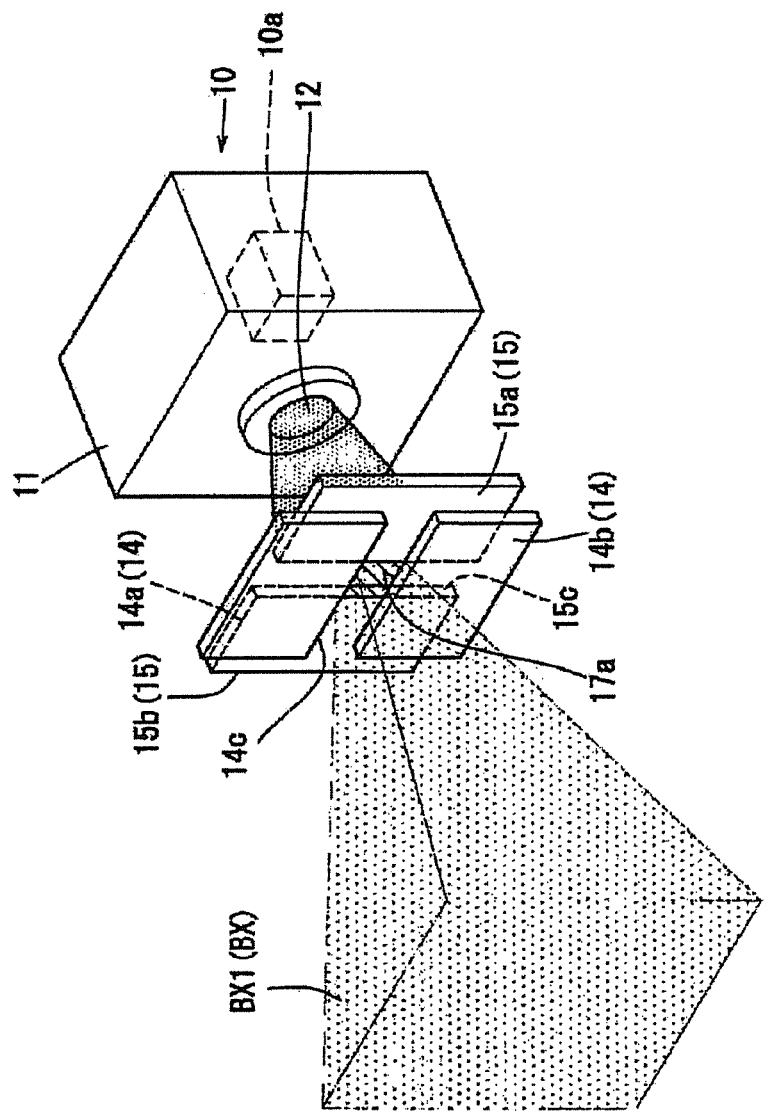
FIG. 6 is a schematic perspective view of an X-ray generation part that emits an X-ray cone beam in which an irradiation range is regulated.
Figure 7:
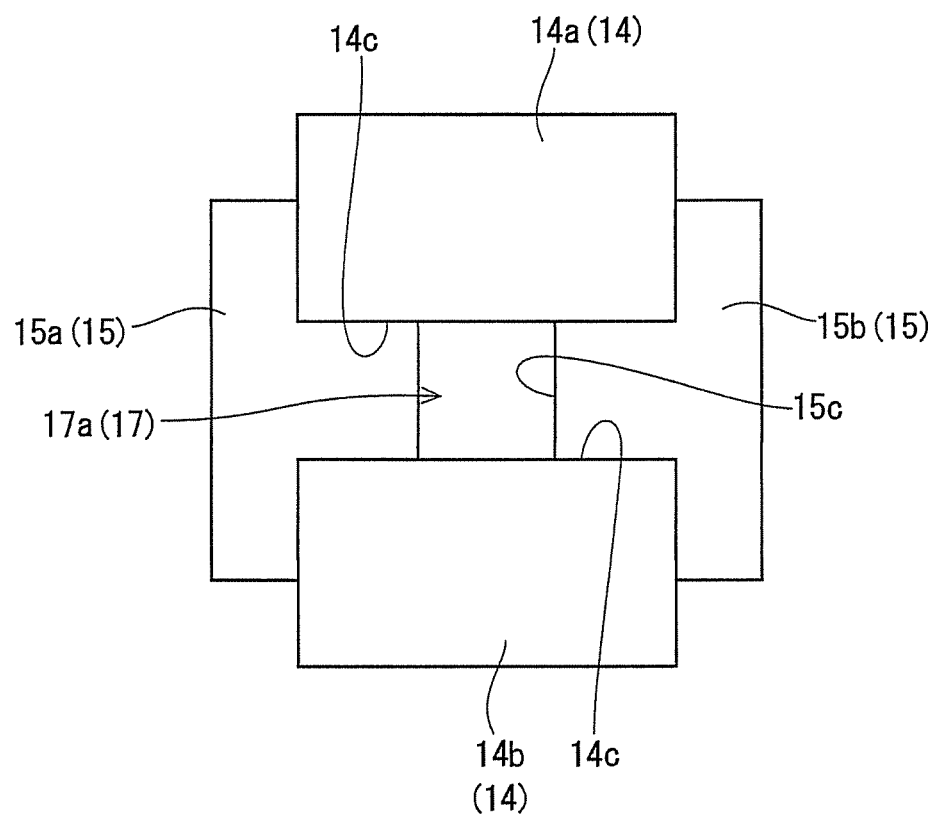
FIGS. 7 and 8 are explanatory views of position adjustments of the vertically-shielding plates and the horizontally-shielding plates.
Figure 8:
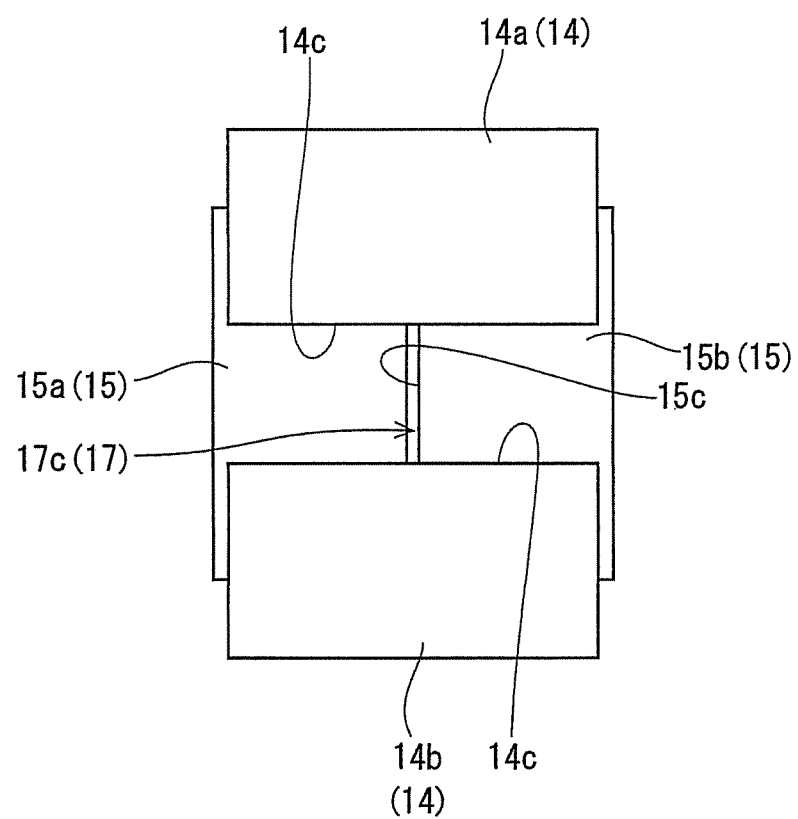

FIG. 5 is a schematic perspective view of the beam forming mechanism 13 (the X-ray regulating part). FIG. 6 is a schematic perspective view of the X-ray generation part 10 that emits the X-ray cone beam in which an irradiation range is regulated. FIGS. 7 and 8 are explanatory views of position adjustments of the vertically-shielding plates 14 and the horizontally-shielding plates 15.

In the turning arm 30, the X-ray generation part 10 that is disposed so as to be opposed to the X-ray detection part 20 includes the X-ray generator 10a including an X-ray tube accommodated in a housing 11 (see FIG. 3). An outgoing port 12 that permits transmission of the X-ray generated by the X-ray tube is provided in a front surface of the housing 11. The beam forming mechanism 13 that acts as the X-ray regulating part is disposed in front (on the front side in FIG. 5 and the side of the −y-direction in the y-axis direction with respect to the X-ray generation part 10) of the outgoing port 12.

The beam forming mechanism 13 includes vertically-shielding plates 14 that move in the vertical direction (the z-axis direction) to shield the X-ray irradiation direction, a horizontally-shielding plates 15 that move in the horizontal direction (the x-axis direction) to shield the X-ray irradiation direction, and a shielding-plate moving mechanism 16 that moves the vertically-shielding plates 14 and the horizontally-shielding plates 15. The shielding-plate moving mechanism 16 is an example of an X-ray-regulating-part drive part 131 illustrated in FIG. 3. An X-ray-regulating-part drive control part 605 of the main body control part 60 controls the drive of the beam forming mechanism 13 (specifically, the shielding-plate moving mechanism 16). The vertically-shielding plates 14 and the horizontally-shielding plates 15 are examples of the X-ray shielding member that is used to regulate a shield amount of the X-ray generated from the X-ray generator 10a in a limited manner.

The vertically-shielding plates 14 include a horizontally-long upper vertically-shielding plate 14a and a horizontally-long lower vertically-shielding plate 14b, which are disposed above and below (the +z side and the −z side) the outgoing port 12 when viewed from the front side. The horizontally-shielding plates 15 include a vertically long, left horizontally-shielding plate 15a and a vertically long, right horizontally-shielding plate 15b, which are disposed on the left and right sides (the −x side and the +x side) of the outgoing port 12 when viewed from the front side. In the example illustrated in FIG. 5, the horizontally-shielding plates 15 are disposed on the side (the −y side) of the housing 11 of the vertically-shielding plates 14. Alternatively, the vertically-shielding plates 14 may be disposed on the side of the housing 11 of the horizontally-shielding plates 15.

The shielding-plate moving mechanism 16 includes a pair of shielding-plate vertically-moving mechanisms 16a that move the upper vertically-shielding plate 14a and the lower vertically-shielding plate 14b in the vertical direction and a pair of shielding-plate horizontally-moving mechanisms 16b that move the left horizontally-shielding plate 15a and the right horizontally-shielding plate 15b in the horizontal direction.

The shielding-plate vertically-moving mechanism 16a includes nut members 141 that are attached to the upper vertically-shielding plate 14a and the lower vertically-shielding plate 14b, vertically-screw shafts 161a that extend vertically to engage the nut members 141, and position adjustment motors 162a (162) that normally or reversely rotate the screw shafts 161a. The screw shaft 161a is normally or reversely rotate by driving the position adjustment motor 162a, whereby the nut member 141 moves up and down along the vertical direction. Therefore, the upper vertically-shielding plate 14a and the lower vertically-shielding plate 14b move independently in the vertical direction. Under the control of the main body control part 60 (specifically, the X-ray-regulating-part drive control part 605), the shielding-plate vertically-moving mechanism 16a adjusts the vertical shielding amount of the X-ray beam emitted from the X-ray generator 10a using the upper vertically-shielding plate 14a and the lower vertically-shielding plate 14b.

The shielding-plate vertically-moving mechanism 16a is an example of a first elevating mechanism, which controls the irradiation direction (the direction in which a center line of an irradiation range extends) by adjusting the spreading (the irradiation range) of the X-ray beam with respect to the vertical direction, namely, a direction with respect to the axial direction of the turning shaft 31.

A regulating cylindrical body 142 is attached to each of the upper vertically-shielding plate 14a and the lower vertically-shielding plate 14b. A through-hole is made in the regulating cylindrical body 142 so as to vertically pierce the regulating cylindrical body 142. A vertically extending regulating shaft 143 is fitted in the regulating cylindrical body 142, and the vertical movement of the regulating cylindrical body 142 is regulated by the regulating shaft 143. Therefore, the upper vertically-shielding plate 14a and the lower vertically-shielding plate 14b move vertically with no inclination.

The shielding-plate horizontally-moving mechanism 16b includes nut members 161 that are attached to the left horizontally-shielding plate 15a and the right horizontally-shielding plate 15b, horizontal screw shafts 161b that extend horizontally to engage the nut members 161, and position adjustment motors 162b (162) that normally or reversely rotate the screw shafts 161b. The screw shaft 161b is normally or reversely rotated by driving the position adjustment motor 162b, whereby the nut member 161 moves right and left along the horizontal direction. Therefore, the left horizontally-shielding plate 15a and the right horizontally-shielding plate 15b move independently in the horizontal direction. Under the control of the main body control part 60, the shielding-plate horizontally-moving mechanism 16b adjusts the horizontal shielding amount of the X-ray beam emitted from the X-ray generator 10a using the left horizontally-shielding plate 15a and the right horizontally-shielding plate 15b. The shielding-plate horizontally-moving mechanism 16b adjusts the irradiation range of the X-ray beam with respect to the horizontal direction.

A regulating cylindrical body 152 is attached to each of the left horizontally-shielding plate 15a and the right horizontally-shielding plate 15b. A through-hole is made in the regulating cylindrical body 152 so as to pierce the regulating cylindrical body 152 in the horizontal direction. A regulating shaft 153 extending horizontally is fitted in the regulating cylindrical body 152, and the horizontal movement of the regulating cylindrical body 152 is regulated by the regulating shaft 153. Therefore, the left horizontally-shielding plate 15a and the right horizontally-shielding plate 15b move horizontally with no inclination.

In the preferred embodiment, the beam forming mechanism 13 includes the vertically-shielding plates 14, the horizontally-shielding plates 15, and the shielding-plate moving mechanism 16, and the beam forming mechanism 13 is disposed in front of the outgoing port 12 in the X-ray generation part 10. Therefore, the irradiation range of the X-ray generated by the X-ray generation part 10 is regulated by the shielding to form the X-ray beam BX1 (the X-ray cone beam) that spreads in a truncated pyramid shape toward the X-ray detection part 20 (see FIG. 6).

Particularly, an interval between opposing edge portions 14c and 14c in the upper vertically-shielding plate 14a and the lower vertically-shielding plate 14b is adjusted by the shielding-plate vertically-moving mechanism 16a, and an interval between opposing edge portions 15c and 15c in the left horizontally-shielding plate 15a and the right horizontally-shielding plate 15b is adjusted by the shielding-plate horizontally-moving mechanism 16b. In order to form the desired-shape X-ray beam, an opening 17, namely, an X-ray opening that has a quadrangular shape when viewed from the front side is formed in front of the X-ray generator 10a by the opposing edge portions 14c and 14c and the opposing edge portions 15c and 15c.

For example, as illustrated in FIG. 7, the interval between the opposing edge portions 14c and 14c is widely adjusted, and the interval between the opposing edge portions 15c and 15c is widely adjusted, whereby the opening 17 becomes a relatively large square opening 17a for large irradiation field when viewed from the front side. The X-ray passing through the opening 17a for large irradiation field has the square section, and becomes the X-ray beam (the X-ray cone beam) that spreads in the square truncated pyramid shape toward the X-ray detection part 20.

As illustrated in FIG. 8, the interval between the opposing edge portions 14c and 14c is widely adjusted, and the interval between the opposing edge portions 15c and 15c is narrowly adjusted, whereby the opening 17 becomes a rectangular, panoramic-photography opening 17c that is vertically long when viewed from the front side. The X-ray passing through the panoramic-photography opening 17c becomes the X-ray slit beam that spreads in the vertically long, truncated pyramid shape toward the X-ray detection part 20.

In the medical X-ray photography apparatus 1, the elevating part 40 and the beam forming mechanism 13 can relatively change the irradiation direction of the X-ray beam BX1 to the head M10 of the subject M1 with respect to the axial direction of the body axis.

The beam forming mechanism 13 in FIGS. 5 to 8 is an example of the irradiation direction changing part. That is, the shape, the quantity, and the moving direction of the shielding plate are not limited to those in the preferred embodiment, but able to be properly changed.

<Photography Mode Selection Screen>

Figure 9:
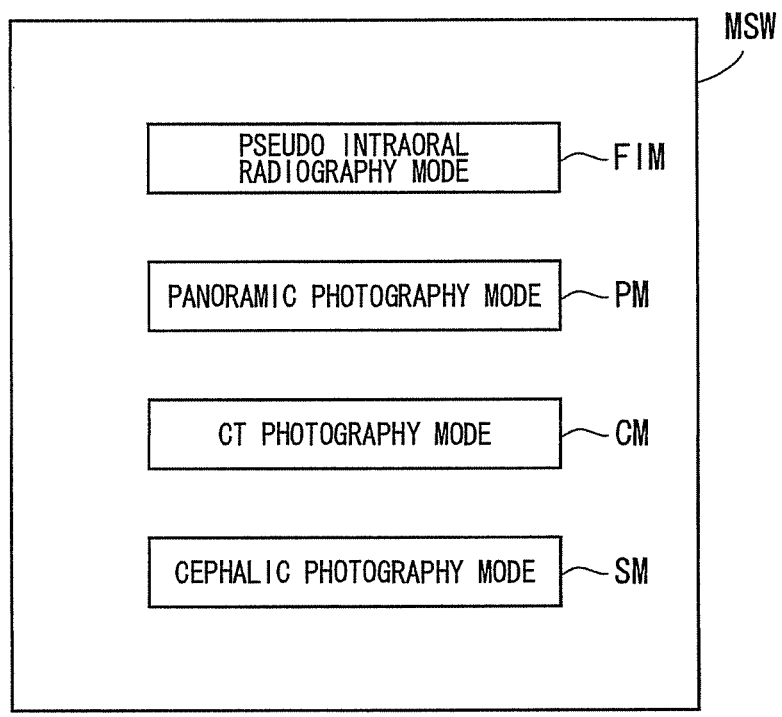
FIG. 9 is a view illustrating a photography mode setting screen used to set a photography mode.

FIG. 9 is a view illustrating a photography mode selection screen MSW used to set a photography mode. The photography mode selection screen MSW illustrated in FIG. 9 includes a pseudo intraoral radiography mode button FIM, a panoramic photography mode button PM, a CT photography mode button CM, and a cephalic photography mode button SM. The pseudo intraoral radiography mode button FIM is used to select a pseudo intraoral radiography mode. The panoramic photography mode button is used to select a panoramic photography mode. The CT photography mode button CM is used to select a CT photography mode. The cephalic photography mode button is used to select a cephalic photography mode.

The photography mode selection screen MSW acts as a photography mode switching part that switches the photography mode performed by the medical X-ray photography apparatus 1.

For example, the photography mode selection screen MSW is displayed on the operation display part 61 or the operation display part 62 before the photographing is performed after the medical X-ray photography apparatus 1 is started up. The operator selects the desired photography mode through the photography mode selection screen MSW. A mode setting part 601 (see FIG. 3) of the main body control part 60 sets the photography mode of the main body control part 60 to the selected photography mode. Therefore, in the medical X-ray photography apparatus 1, a photographing condition (such as the position and the shape of the photographic region) can be set according to the X-ray photography of the set type.

The pseudo intraoral radiography mode is one in which the pseudo intraoral radiography is performed. In the pseudo intraoral radiography, the conventional intraoral radiography (the dental radiography) in which the partial region (for example, a few teeth) of the row of teeth is set to the photographing target is performed in the pseudo manner with the medical X-ray photography apparatus 1. At this point, the X-ray image obtained by the conventional intraoral radiography is a simple projection image, which is obtained by irradiating the partial region of the row of teeth with the X-ray in one direction while the conventional X-ray film is mounted in the mouth cavity. On the other hand, in the pseudo intraoral radiography, the image equivalent to the simple projection image or the image with which the equivalent diagnosis can be made is generated by the tomographic image. The pseudo intraoral radiography is described in detail later.

The panoramic photography mode is one in which the panoramic photography (panoramic X-ray photography) is performed. In the panoramic photography, the row of teeth is irradiated along a dental arch with the X-ray beam formed into the X-ray slit beam, thereby obtaining the frame data. The information processing device 8 (the image processor 801) generates one panoramic image (the panoramic X-ray image) by connecting end portions of the projection images expressed by the frame data (however, generation of an overlapping portion is not troublesome).

In the panoramic photography, the row of teeth is irradiated with the X-ray slit beam such that the dental arch is traced. At this point, preferably the row of teeth is irradiated with the X-ray slit beam such that a center axis of the X-ray slit beam is always orthogonal to a curve of the dental arch. Therefore, the turning shaft 31 is properly displaced in the direction (the direction parallel to the XY plane) orthogonal to the axial direction of the turning shaft 31 by the moving part 202 while the turning arm 30 is turned by the turning part 201, and the row of teeth is irradiated with the X-ray slit beam such that a moving trajectory of the X-ray slit beam forms an envelope. Japanese Patent Application Laid-Open No. 2011-152411 discloses the movement of the X-ray slit beam in the panoramic photography, and the content of Japanese Patent Application Laid-Open No. 2011-152411 can be applied to the medical X-ray photography apparatus 1 by reference.

The CT photography mode is one in which the CT photography is performed. In the CT photography, the X-ray beam is formed in which the irradiation range is regulated so as to include the whole photographic region (the CT photographic region). The photographic region is irradiated with the X-ray beam in multiple directions (for example, the directions of at least 180 degrees) to obtain the frame data. The information processing device 8 (the image processor 801) reconstructs the tomographic image of the specific cutting plane by applying the filter back projection method (FBP method) to the obtained frame data.

The cephalic photography mode is one in which the cephalic photography is performed. In the cephalic photography, as illustrated in FIG. 2, the cephalic unit 43 is mounted on the medical X-ray photography apparatus 1, and the head M10 of the test subject is irradiated with the X-ray slit beam formed for the purpose of the cephalic photography to obtain the frame data. A cephalic photography X-ray detector 432 is configured to be able to be displaced in the Y-direction. The shielding-plate moving mechanism 16 is actuated to scan the head M10 in the Y-direction with the X-ray slit beam, the cephalic photography X-ray detector 432 is displaced in synchronization with the scanning of the head M10, and the cephalic photography X-ray detector 432 acquires the frame data while always receiving the X-ray slit beam during the cephalic photography. The information processing device 8 (the image processor 801) generates one projection image (a head X-ray standard image) of the whole head M10 by connecting end portions of the projection images expressed by the obtained frame data (however, generation of an overlapping portion is not troublesome).

In the case that the panoramic photography mode is selected, the panoramic photography mode may progress to a target region-specific photography mode selection screen on which a whole region panoramic photography mode and a partial panoramic photography mode can be selected.

As used herein, the whole region panoramic photography mode is one in which the whole region of a jaw bone is set to the target region of the panoramic photography, and the partial panoramic photography mode is one in which the partial region of the jaw bone is set to the target region of the panoramic photography.

In the case that the CT photography mode is selected, the CT photography mode may progress to a target region-specific photography mode selection screen on which a whole region CT photography mode and a partial CT photography mode can be selected. As used herein, the whole region CT photography mode is one in which the whole region of the jaw bone or the whole region of the dental arch is set to the target region of the CT photography, and the partial CT photography mode is one in which the partial region of the jaw bone or the partial region of the dental arch is set to the target region of the CT photography.

<Photographic Region Setting Screen>

Figure 10:
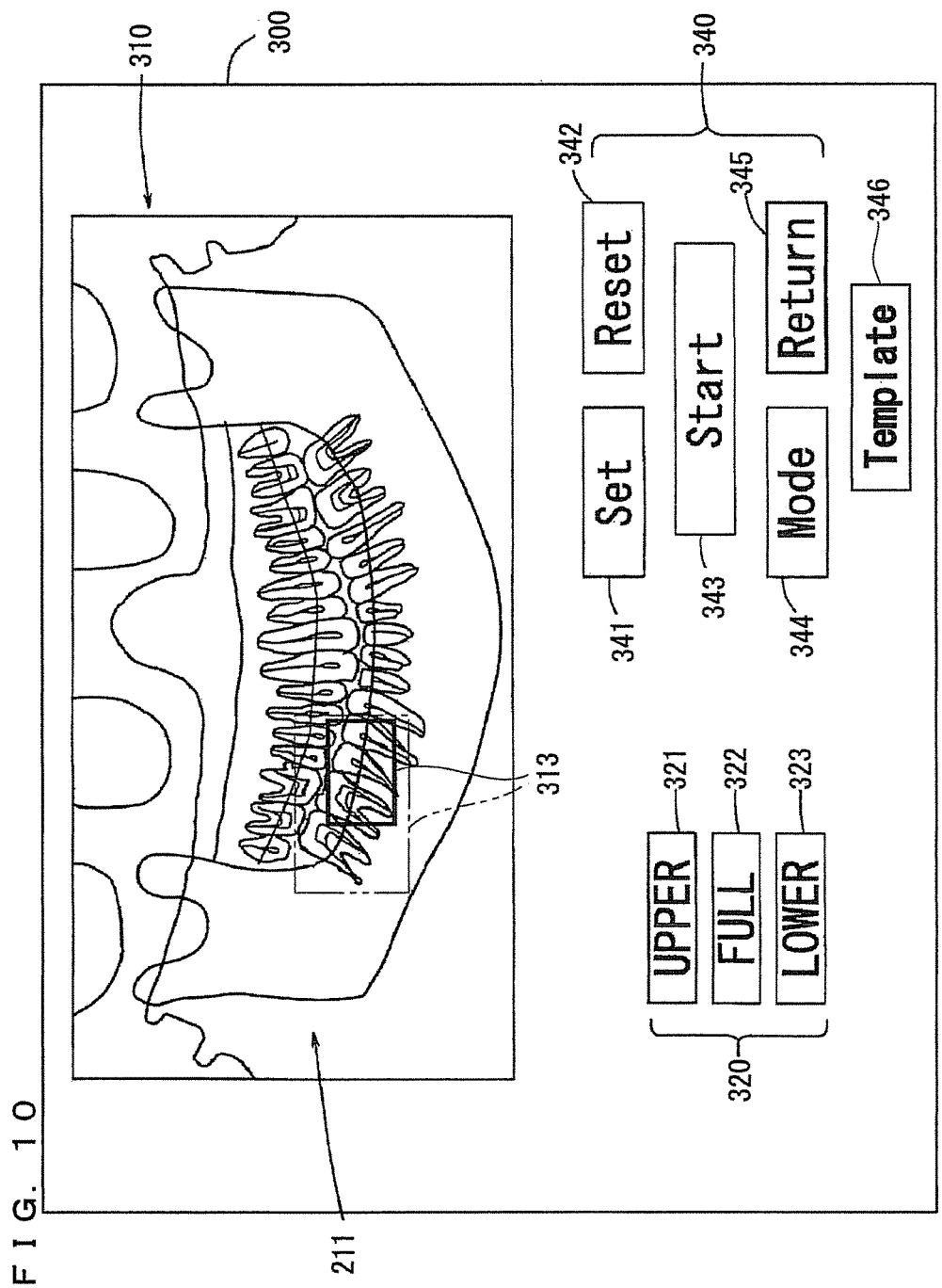
FIG. 10 is a view illustrating a photographic region setting screen used to set a photographic region.

FIG. 10 is a view illustrating a photographic region setting screen 300 used to set the photographic region CA. The photographic region setting screen 300 illustrated in FIG. 10 includes an image display portion 310, an upper and lower jaw selection portion 320, a selection range setting portion 330, and a condition setting portion 340. The condition setting portion 340 includes a set button 341, a reset button 342, a start button 343, a mode button 344, and a return button 345.

In each mode that can be selected on the photography mode selection screen MSW in FIG. 9, the photographic region setting screen 300 is commonly or substantially commonly used particularly in the pseudo intraoral radiography mode, the panoramic photography mode, and the CT photography mode.

The dental arch viewed in the Y-axis direction, specifically the image (a panoramic image 211) viewed in a direction from a −Y-side toward a +Y-side and a photographic region line 313 are displayed on an image display portion 310 while superimposed on each other. In the panoramic image, the jaw bone is usually displayed in such a direction as to be observed from the front surface. Therefore, in the panoramic image 211 displayed on the image display portion 310, the right side of the jaw bone is located on the left side on the screen while the left side of the jaw bone is located on the right side on the screen. The photographic region line 313 is set to the proper size by operating the photographic region line 313 using the mouse of the information processing device 8, and the X-ray-regulating-part drive part may be driven in conjunction with the set size.

The mode selection button 344 is used to select various modes. For example, in the case that the pseudo intraoral radiography is performed, the pseudo intraoral radiography mode is selected using the mode selection button 344. Then, the size of the photographic region line 313 may arbitrarily be adjusted according to the photographing purpose, or the photographic region line may automatically be moved by default state in response to a signal transmitted from an input part based on a tooth number or an illustration illustrating each locus of the row of teeth.

The upper and lower jaw selection portion 320 includes an UPPER button 321, a FULL button 322, and a LOWER button 323. The UPPER button 321 sets the photographic region CA to the upper jaw region. The FULL button 322 sets the photographic region CA to both the upper jaw region and the lower jaw region. The LOWER button 323 sets the photographic region CA to the lower jaw region.

Through the upper and lower jaw selection portion 320, for example, when the CT photography mode is selected using the mode selection button 344, the photography mode of the main body 2 is set to one of the CT photography mode (a first CT photography mode) in which the region extending across the upper jaw and the lower jaw is set to the target region of the CT photography and the CT photography mode (a second CT photography mode) in which one of the regions of the upper jaw and the lower jaw is set to the target region of the CT photography.

Depending on the selected photography mode, the photographic region selected by the upper and lower jaw selection portion 320 is set to one of the whole region and the partial region of the upper jaw, the lower jaw, and the upper and lower jaws. For example, when the upper jaw region is selected while the partial panoramic photography mode or the partial CT photography mode is selected, the part of the upper jaw is the photographic region. When the upper jaw region is selected while the whole region panoramic photography mode or the whole region CT photography mode is selected, the whole region of the upper jaw is the photographic region.

When the FULL button 322 is pressed while the whole region panoramic photography mode is selected, the conventionally well-known entire jaw panoramic photography is performed. Because the pseudo intraoral radiography mode is one in which the pseudo intraoral radiography is performed, the photography target region is the partial region.

The mode selection performed using the mode selection button 344 may be received prior to or subsequent to the photographic region setting performed on the photographic region setting screen 300.

The condition setting portion 340 is constructed by the set button 341, the reset button 342, the start button 343, the mode button 344, and the return button 345. The set button 341 is operated to determine a designation content of the photographic region CA. The designation content of the photographic region CA is set through the image display portion 310 and the upper and lower jaw selection portion 320. The reset button 342 is operated to reset the designation content of the photographic region CA, which is set through the image display portion 310 and the upper and lower jaw selection portion 320.

The start button 343 is operated to provide a designation to start the X-ray photography of the photographic region CA based on the designation content fixed by the set button 341. The mode button 344 is operated to select various modes. When the mode button 344 is operated to be selected, the modes that can be selected on the photography mode selection screen MSW in FIG. 9 can directly be changed and selected without tentatively displaying the photography mode selection screen MSW. The mode button 344 is a button that switches among the pseudo intraoral radiography mode, the CT photography mode, the panoramic photography mode, and the cephalic photography mode. That is, the mode button 344 acts as a photography mode switching part that switches the photography mode performed by the medical X-ray photography apparatus 1. The return button 345 is operated to return to an initial screen (for example, photography mode selection screen MSW illustrated in FIG. 9).

The photographic region CA of the X-ray photography can be set on the photographic region setting screen 300. In order to set the photographic region CA, the photographic region line 313 is set in the photographic region setting screen 300 displayed on the operation display part 61 so as to surround a photographing target object. Particularly, one of the upper jaw, the lower jaw, and the upper and lower jaws is selected in the upper and lower jaw selection portion 320 according to the position of the photographing target object. In the panoramic image 211 displayed on the image display portion 310, a designation cursor 312 is moved by a predetermined operation (for example, a drag and drop operation using the mouse) to assign the photographic region line 313. The position and size of the photographic region line 313 are arbitrarily changed as illustrated by a solid line and an alternate long and two short dashes line in FIG. 10 such that the desired photographing target object is surrounded by the photographic region line 313.

Even if one of the upper jaw, the lower jaw, and the upper and lower jaws is tentatively selected by the upper and lower jaw selection portion 320, the photographic region line 313 may be moved by the operation of the designation cursor 312 such that another region is set to the photography target region.

In the image display portion 310, designation information that is input to designate the photographic region CA with respect to the panoramic image 211 is transmitted to the information processing device 8. The information processing device 8 transmits the information on the photographic region line 313 corresponding to the received designation information to the operation display part 61.

The operation display part 61 that receives the information on the photographic region line 313 displays the panoramic image 211 and the photographic region line 313 based on the received information in the image display portion 310 of the photographic region setting screen 300 while superimposing the panoramic image 211 and the photographic region line 313 on each other.

Thus, on the photographic region setting screen 300, a length along the dental arch in the photographic region CA can arbitrarily be set by scaling the range surrounded by the photographic region line 313 in the direction (the crosswise direction) along the row of teeth. A height orthogonal to the dental arch can arbitrarily be set by scaling the range surrounded by the photographic region line 313 in the direction (the vertical direction) orthogonal to the direction along the row of teeth. One of the lengths in the vertical direction and the horizontal direction may be fixed with respect to the photographic region line 313.

For the pseudo intraoral radiography, the tooth included in the set photographic region CA is the photographing target. Accordingly, the operation display part 61 (or the operation display part 62) acts as a photographic region assignment receiving part 610 (see FIG. 3) that receives the operation to designate the photographic region of the pseudo intraoral radiography. The photographic region assignment receiving part 610 can assign the part of the row of teeth along the dental arch as the photographic region.

The operation display part 61 (or the operation display part 62) includes the touch panel, and the setting operation of the photographic region CA is received by operating the designation cursor 312 displayed on the photographic region setting screen 300. Alternatively, the operation display part 61 may include a liquid crystal screen, and the setting operation of the photographic region CA may be received through a pointing device such as a mouse or an operation button placed near the operation display part 61.

The photographic region setting screen 300 is an example of the setting screen of the photographic region CA, and can properly be changed. For example, an illustration representing the panoramic image or an illustration representing the dental arch may be displayed instead of the panoramic image 211, and the photographic region line 313 may be set on the illustration.

The jaw may be previously defined while divided into relatively narrow regions (each range including one to three teeth), and the operator may select the defined region to set the photographic region CA. In the case that for example, the previously-defined region is displayed on the image representing the dental arch while surrounded by a frame, the setting work of the photographic region CA can easily be performed by selecting one or a plurality of regions surrounded by the frames.

Figure 11A:
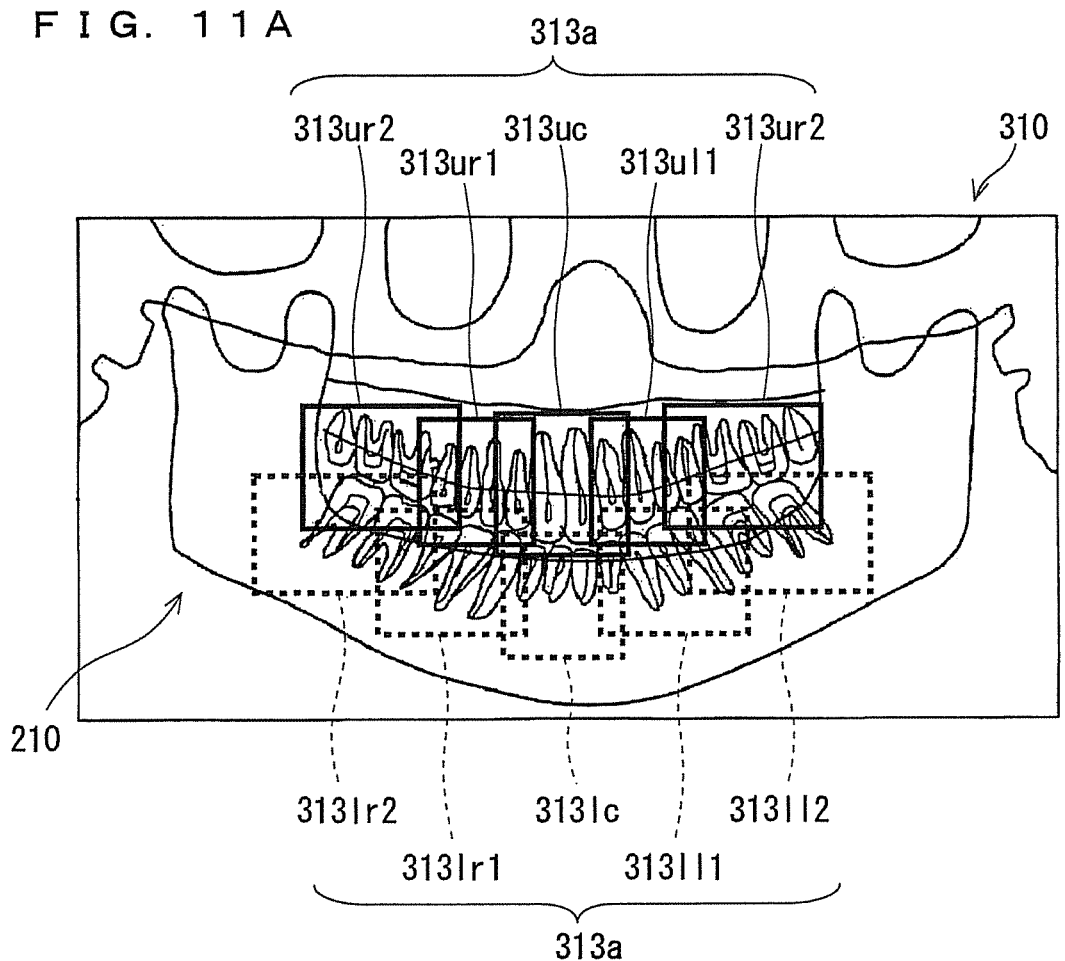
Figure 11B:
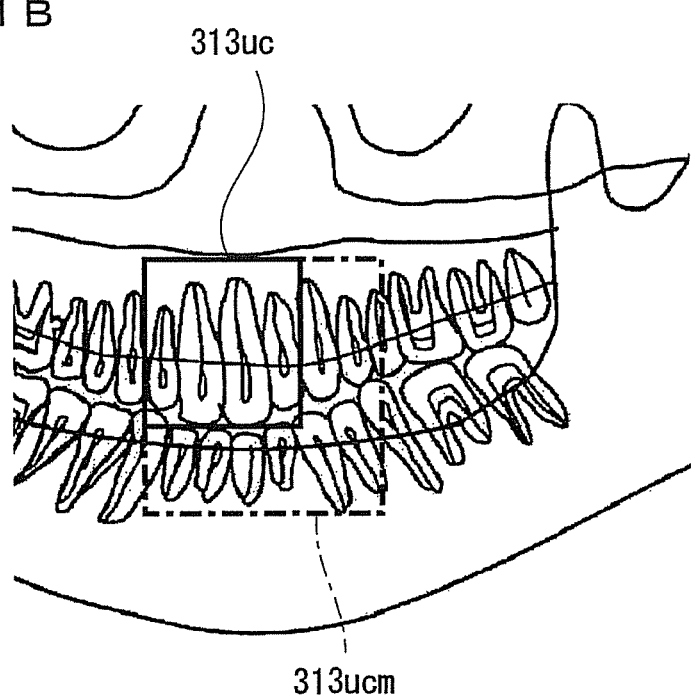

FIGS. 11A and 11B are views illustrating other examples of the image display portion 310. Although FIGS. 11A and 11B are similar to FIG. 10 in the display of the panoramic image 211, FIGS. 11A and 11B are different from FIG. 10 in that the photographic region line 313 is previously superimposed on the panoramic image 211 as a template constructed by a photographic region selection line 313*a* including a plurality of rectangular frame lines.

Ten frames are prepared in total as the photographic region selection lines 313*a*, and the selection of one of the frames is received. Similarly to FIG. 10, the illustration of the entire jaw panoramic image may be used instead of the panoramic image. In the photographic region selection lines 313a, the regions are set based on a 10-film method of the well-known intraoral radiography. The photographic region selection line 313a is configured to indicate the region irradiated with the X-ray cone beam. In the setting by the region selection, preferably, a photographic region that is the same or approximately same as the photographic region of the 10-film method of the well-known intraoral radiography is set. The purpose of the pseudo intraoral radiography in this invention is to obtain an image similar to an image by conventional intraoral radiography, so the word "pseudo" having been described above can be converted to "imitative", "simulated" or "emulation". Therefore, the word "pseudo intraoral radiography" can be converted to the word "imitative intraoral radiography", "simulated intraoral radiography" or "emulation intraoral radiography"

The region irradiated with the X-ray cone beam is the rectangle due to the structure of the beam forming mechanism 13 in FIG. 5, and it is structurally advantageous when the rectangular irradiated region is not tilted. Therefore, the photographic region selection line 313a is displayed on the image display portion 310 in the rectangular shape that is not tilted.

In the photographic region selection line 313a, the region including anterior teeth on the right and left of the upper jaw is set to a region 313uc, the row of teeth on the left side of the upper jaw is set to regions 313ul1 and 313ul2 from the anterior tooth side toward a left molar tooth side, and the row of teeth on the right side of the upper jaw is set to regions 313ur1 and 313ur2 from the anterior tooth side toward a right molar tooth side.

The same holds true for the row of teeth of the lower jaw. The region including anterior teeth on the right and left of the lower jaw is set to a region 313lc, the row of teeth on the left side of the lower jaw is set to regions 313ll1 and 313ll2 from the anterior tooth side toward the left molar tooth side, and the row of teeth on the right side of the lower jaw is set to regions 313lr1 and 313lr2 from the anterior tooth side toward the right molar tooth side.

The operator can selectively assign the desired region from the regions 313uc, 313ul1, 313ul2, 313ur1, 313ur2, 313lc, 313ll1, 313ll2, 313lr1, and 313lr2. For example, the selection and assignment are performed by touching one of the frames of the photographic region selection line 313a on the display in the configuration in which the touch panel is used, and the selection and assignment are performed by operating a pointer using the mouse in the configuration in which the mouse is used.

When the operation to deform the photographic region selection line 313a in FIG. 11A is received, the pseudo intraoral radiography region CA may be changed in conjunction with the deformation. For example, as illustrated in FIG. 11B, when the operation to move the position in the lower right corner of the photographic region selection line 313uc to the further lower right is received, the whole of the photographic region selection line 313uc is deformed so as to become a photographic region selection line 313ucm enlarged toward the lower right.

The above deformation operation is described in accordance with the right and left directions in FIGS. 11A and 11B. When the deformation operation is described in accordance with the right and left directions of the jaw bone, the deformation operation is described as follows. That is, when the operation to move the position in the lower left corner of the photographic region selection line 313uc to the further lower left is received, the whole of the photographic region selection line 313uc is deformed so as to become the photographic region selection line 313ucm enlarged toward the lower left.

The beam forming mechanism 13 (the X-ray regulating part) in FIG. 5 is driven in conjunction with the deformation, the shape of the opening 17, namely, the X-ray opening is changed, the regulation of the X-ray cone beam BX1 is adjusted to enlarge the irradiation range, and the pseudo intraoral radiography region CA is changed and enlarged. The same holds true for the reduction. The deformation may be performed only in the vertical direction or the horizontal direction.

FIG. 11B illustrates an example of the size change in the deformation of the template. In the operation to deform the photographic region selection line 313a, the portion to be moved in the frame line of the photographic region selection line 313a can be moved by the operation to touch the touch panel or the pointer operation. The conjunction is not necessarily performed at the same time, but the pseudo intraoral radiography region CA may be performed after, for example, a decision operation is received.

The scaling of the template is performed by another method except the method for changing the pseudo intraoral radiography region CA by driving the beam forming mechanism 13. For example, the position of the turning center of the turning arm 30 in the pseudo intraoral radiography is changed by the moving mechanism 200 in conjunction with the deformation of the photographic region selection line 313a, the pseudo intraoral radiography region CA is enlarged by bringing the X-ray detector 21 close to the photography target region, and the pseudo intraoral radiography region CA may be reduced by distancing the X-ray detector 21 from the photography target region, namely, by adjusting the proximity.

The pseudo intraoral radiography region CA may be changed by driving the beam forming mechanism 13 at the same time as the pseudo intraoral radiography region CA is changed by bringing or distancing the X-ray detector 21 close to or from the photography target region.

Specifically, the change of the pseudo intraoral radiography region CA, which is by bringing or distancing the X-ray detector 21 close to or from the photography target region, will supplementally be described subsequent to the description of moving control of the turning arm 30 in FIG. 15.

In the examples in FIGS. 11A and 11B, the 10-film method is adopted as the multiple-photographing method. Alternatively, another multiple-photographing method may be adopted.

FIG. 12 is a view illustrating another example of the image display portion 310. FIG. 12 illustrates a modification in which a multiple-photographing method different from that in the image display portion 310 of the photographic region setting screen 300 in FIG. 11A is adopted. The photographic region selection line 313a set in FIG. 12 differs from the photographic region selection line 313a set in FIG. 11A in that the photographic region selection line 313a set in FIG. 12 is the region based on a 14-film method of the well-known intraoral radiography.

Fourteen frames are prepared in total as the photographic region selection lines 313a, and the selection of one of the frames is received. In the photographic region selection line 313a, the region including anterior teeth on the right and left of the upper jaw is set to a region 313uc, the row of teeth on the left side of the upper jaw is set to regions 313ul1, 313ul2, and 313ul3 from the anterior tooth side toward a left molar tooth side, and the row of teeth on the right side of the upper jaw is set to regions 313*ur*1, 313*ur*2, and 313*ur*3 from the anterior tooth side toward a right molar tooth side.

The same holds true for the row of teeth of the lower jaw. The region including anterior teeth on the right and left of the lower jaw is set to a region 313*lc*, the row of teeth on the left side of the lower jaw is set to regions 313*ll*1, 313*ll*2, and 313*ll*3 from the anterior tooth side toward the left molar tooth side, and the row of teeth on the right side of the lower jaw is set to regions 313*lr*1, 313*lr*2, and 313*lr*3 from the anterior tooth side toward the right molar tooth side.

The operator can selectively assign the desired region from the regions 313*uc*, 313*ul*1, 313*ul*2, 313*ul*3, 313*ur*1, 313*ur*2, 313*ur*3, 313*lc*, 313*ll*1, 313*ll*2, 313*ll*3, 313*lr*1, 313*lr*2, and 313*lr*3.

The touch panel used to select the photographic region selection line 313*a* is the photography locus selector that selects any locus.

The photographing method may be configured to be able to be selected from different multiple-photographing methods. For example, the photographic region selection line 313*a* in FIG. 11A and photographic region selection line 313*a* in FIG. 12 may be displayed so as to be able to be switched. That is, it can be configured such that the photographing method modes such as the 10-film method and the 14-film method can be prepared and selected according to the diagnostic purpose, and various templates are arranged and disposed based on the selected photographing method. There is a case that the 10-film method and the 14-film method are expressed as "10-film survey", "14-film survey". Conventionally, films were used in these multiple-photographing methods. Therefore, the term "film" is used in these multiple-photographing methods. The pseudo intraoral radiography is an X-ray photography of which the photographic region is the same or approximately same as the photographic region of the intraoral radiography and which is performed by a tomography of an extra-oral radiography so that a tomographic image is generated instead of a X-ray image by the intraoral radiography.

A template mode switch 346 in FIG. 10 may be used to start up the template mode that is of a multiple-photographing method photographic region selection mode in which the photographic region selection line 313*a* is used as the template. The template mode switch 346 may be also used to select the multiple-photographing methods such as the 10-film method mode and the 14-film method mode in the template mode.

Figure 13:
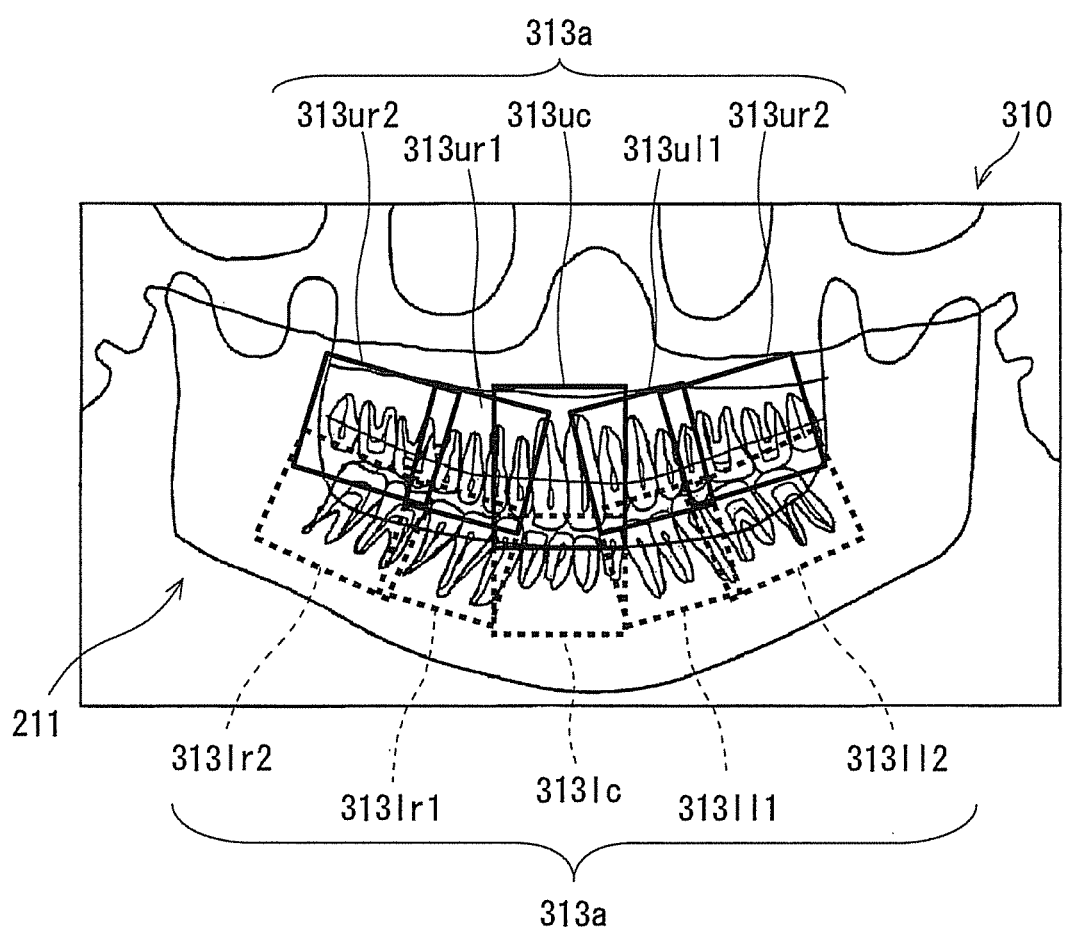

The 14-film method is less than the 10-film method in an X-ray exposure dose, while the 14-film method is narrower than the 10-film method in the photographic region. The rectangular photographic regions may horizontally be arranged as illustrated in FIGS. 11A, 11B and 12, or the rectangular photographic regions may be arranged along an occlusion line that is gently curved into a U-shape as illustrated in FIG. 13. According to the multiple-photographing method mode, such as the 10-film method and the 14-film method, which is selected by the template mode switch 346 and the selected photographic region selection line, the turning arm moves to the photography starting position previously stored in the storage part in response to the photography starting signal, and the X-ray photography is performed. When the turning arm reaches the photography ending position previously stored in the storage part, the turning arm stops the movement, and the X-ray photography is ended.

The template mode switch 346 is an element constituting the photographic region assignment receiving part 610. That is, the template mode switch 346 acts as the multiple-photographing method photographic region selection mode start-up part, and also acts as the multiple-photographing method selection switch, namely, the multiple-photographing method selector.

The shape and size of the cursor of the template are determined according to the multiple-photographing method mode selected by the template mode switch 346 that acts as the multiple-photographing method selector.

The prepared modes are not limited to the 10-film method and the 14-film method, but it is conceivable to combine various multiple-photographing methods. The operator may set and store the template having any pattern.

FIG. 13 is a view illustrating another example of the image display portion 310. The photographic region selection line 313*a* in FIG. 13 differs from the photographic region selection line 313*a* in FIG. 11A in that the photographic region selection line 313*a* in FIG. 13 does not always indicate the region to which the X-ray irradiation is actually performed, but the region of the 10-film method of the well-known intraoral radiography is directly displayed. Therefore, the photographic region selection lines 313*a* in FIG. 13 include the inclined rectangular frames such as the frames 313*ul*1, 313*ul*2, 313*ll*1, and 313*ll*2.

Although the actual irradiation region with the X-ray cone beam is the region in FIG. 11A, the region in FIG. 13 is displayed such that the operator can select the region in a familiar manner.

Similarly to the case in FIG. 11A, another multiple-photographing method may be selected in addition to the 10-film method. The photographic region selection line 313*a* in FIG. 13 and the photographic region selection line 313*a* of another multiple-photographing method may be switched similarly to the case in FIG. 11A.

Figure 14:
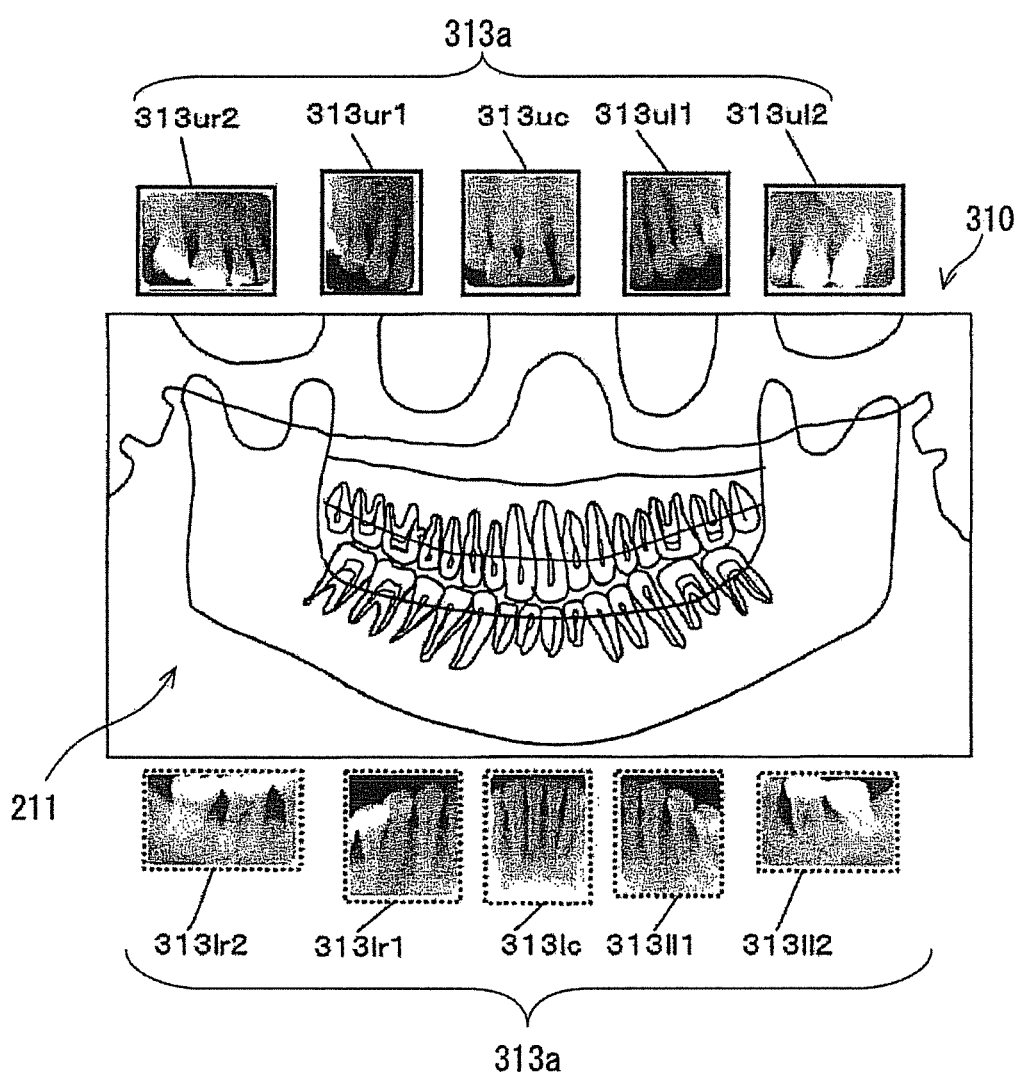

FIG. 14 is a view illustrating the image display portion 310 according to a modification.

The photographic region selection line 313*a* in FIG. 14 differs from the photographic region selection line 313*a* in FIG. 11A in that the photographic region selection line 313*a* in FIG. 14 is not displayed while overlapping with the panoramic image 211, but the photographic region selection line 313*a* in FIG. 14 is displayed around the panoramic image 211 according to the position of the actual locus.

In the example in FIG. 14, as to the row of teeth of the upper jaw, the anterior tooth of the upper jaw is displayed in the upper center of the panoramic image 211, the left molar tooth region is displayed on the right so as to be arranged toward the upper screen of the panoramic image 211, and the right molar tooth region is displayed on the left so as to be arranged toward the upper screen of the panoramic image 211. The same holds true for the row of teeth of the lower jaw.

In the photographic region selection line 313*a* in FIG. 14, the regions identical to those in FIG. 11A indicated by the same numerals are set, and the image of the tooth in the region photographed by the intraoral radiography of the general 10-film method.

The tooth image displayed in the frame may be an image example of the typical tooth of each region, an actual X-ray photograph, or a schematic diagram expressed by the illustration. Similarly to the case in FIG. 11A, another multiple-photographing method may be selected in addition to the 10-film method. The photographic region selection line 313*a* in FIG. 14 and the photographic region selection line 313*a* of another multiple-photographing method may be switched similarly to the case in FIG. 11A.

In the display modes in FIGS. 10, and 11A to 14, at least a plurality of display modes may be displayed at the same time, or at least a plurality of display modes may be displayed while being able to be switched. For example, it can be configured such that, in addition to the display in FIG. 10, the photographic region line 313 in FIGS. 11A and 11B can be displayed, the previously-prepared plurality of photographic region selection lines 313a can be used, and the photographic region line 313 of the desired position and shape can be assigned.

In another configuration example, the photographic region selection line 313a in FIGS. 11A and 11B or the photographic region selection line 313a in FIG. 13 may be displayed at the same time as the photographic region selection line 313a in FIG. 14. When one of the frames in the photographic region selection line 313a in FIG. 14 is selected or tentatively selected, only the frame that is selected or tentatively selected in the photographic region selection line 313a in FIGS. 11A and 11B or photographic region selection line 313a in FIG. 13 may simultaneously be displayed.

For example, it is assumed that the photographic region selection line 313a is displayed in the display mode in FIG. 14. For example, when the frame 313uc is selected or tentatively selected, the corresponding frame 313uc in the photographic region selection line 313a in FIG. 13 emerges, and the frame 313uc is displayed while overlapping with the panoramic image 211.

In the configuration example, when one of the photographic region selection line 313a of the display mode in FIG. 14 and the photographic region selection line 313a of the display mode in FIG. 13 is deformed, the other may be deformed according to the deformation.

As used herein, the "tentative selection" means, in the configuration in which the photographic region assignment receiving part 610 is moved by the pointer using the mouse, for example, the click is not performed but the pointer is placed on any portion of the photographic region selection line 313a.

<Pseudo Intraoral Radiography>

FIG. 15 is a schematic plan view illustrating a situation of the pseudo intraoral radiography when viewed in the −Z-direction from the +Z-side. In FIG. 15, a plurality of teeth on the right side in the lower jaw are set to the photographing target. The teeth that are of the photographing target are designated through the photographic region setting screen 300 illustrated in FIG. 10.

As illustrated in FIG. 15, in the pseudo intraoral radiography, like the conventional tomosynthesis, the X-ray generator 10a and the X-ray detector 21 are turned while the head M10 of the subject M1 is interposed therebetween, thereby the photographing target object (in this case the plurality of teeth) is irradiated with the X-ray beam BX1 in multiple directions.

More specifically, the X-ray beam in which the irradiation range is regulated so as to include the whole photographic region (the pseudo intraoral radiography region CA) is formed in the pseudo intraoral radiography. The photographic region is irradiated with the X-ray beam in a plurality of directions (the directions within a predetermined range) to obtain the frame data. The information processing device 8 (image processor 801) performs the image processing on the obtained frame data to obtain the tomographic image of the target tomographic plane. In the image processing, for example, a shift-and-add method is applied to stacking (overlapping) the X-ray projection images expressed by the frame data, thereby reconstructing the tomographic image. Although a character of the reconstructed tomographic image in this manner differs strictly from that of the X-ray image obtained by the conventional intraoral radiography, the reconstructed tomographic image is extremely close to the X-ray image obtained by the conventional intraoral radiography from the viewpoint of the image diagnosis.

As used herein, the "shift-and-add method" means a method in which the tomographic image having any height is obtained by stacking the projection images that are obtained by changing the X-ray irradiation direction. Specifically, the X-ray passing through the common position of the target tomographic plane is photographed at the different position in each piece of frame data by changing the X-ray irradiation direction. Therefore, the pieces of frame data are shifted and overlapped such that the different positions are matched with each other, which allows the target tomographic plane to be highlighted.

The method for generating the tomographic image is not limited to the shift-and-add method. For example, the tomographic image may be reconstructed by filter back projection used in the reconstruction of the CT image or similar back projection.

The tomographic images of a plurality of types may be reconstructed by performing both the shift-and-add method and the filter back projection or the similar back projection, and simultaneously or alternately displayed. For example, when a filter function is selected so as to be focused on the specific tomographic plane, the tomographic image having the excellent contrast can be obtained. At the same time, the information content of the portion before and behind the tomographic plane increase to degrade the contrast. However, for example, a metallic artifact is hardly generated, so that the tomographic image suitable for the diagnosis can be obtained. Thus, the diagnostic imaging can effectively be performed by performing the pieces of image processing having different information content on the X-ray absorption of the portion before and behind the specific tomographic plane.

In the above example, the irradiation field of the X-ray beam in which the irradiation range is regulated includes the whole of the photographic region (the pseudo intraoral radiography region CA). Alternatively, for example, the horizontal width of the X-ray beam BX1 may be further narrowed to form the X-ray slit beam used in the panoramic photography, and the photographic region may horizontally be scanned. That is, the pseudo intraoral radiography may be performed by the X-ray photography similar to the panoramic photography to the pseudo intraoral radiography region CA, which is a kind of a restricted region. However, when the spread of the X-ray beam BX is wider than at least the photographic region CA, the X-ray projection image data having wealth of information on X-ray absorption in the photographic region CA can be collected even at the small turning angle. Therefore, the tomographic image can be generated without trouble.

In reconstructing the tomographic image, the position and shape of the cutting plane can arbitrarily be determined by the reconstruction calculation method, namely, by properly changing the shift amount for the stacking. For example, as illustrated in FIG. 15, the cutting plane can be set to the planar cutting plane A1, and also set to a curved cutting plane A2 in accordance with a dental arch 90 along the row of teeth. For example, the cutting plane is moved to a buccal-lingual direction Dr1 orthogonal to the dental arch 90 by a predetermined operation to set a new curved cutting plane A3. The buccal-lingual direction Dr1 means a direction from the cheek side toward the tongue side or the opposite direction thereto.

The whole position of the dental arch 90 set in the image processing may be corrected. For example, as indicated by RV in FIG. 15, the position of the dental arch 90 is corrected in the Y-axis direction. The reconstructed position is adjusted in the Y-axis direction by the correction. For example, the operator can perform the adjustment while viewing a degree of image formation.

In the pseudo intraoral radiography, the moving control of the turning arm 30 can be performed by the setting of the turning center of the turning shaft moving control in order to irradiate the target photographic region CA, in which the planar cutting plane A1 and the curved cutting plane A2 are set, with X-ray cone beam BX1. In this case, for example, the turning center is set to a central portion A1C viewed in the Z-direction of the planar cutting plane A1 or a central portion A2C viewed in the Z-direction of the curved cutting plane A2. The shaft center 31C of the turning shaft 31 that is of the mechanical shaft member turns about the central portion A1C as illustrated in FIG. 15. The shaft center 31C may rotate about the central portion A2C.

During the X-ray photography, a cutting plane thickness (a tomographic thickness) can be changed within a predetermined range by changing the turning angle of the turning arm 30. Specifically, the tomographic thickness of the buccal-lingual direction Dr1 decreases with increasing turning angle of the turning arm 30, and the tomographic thickness increases with decreasing turning angle. The photographic region assignment receiving part 610 may receive the assignment of the tomographic thickness. In this case, the photographic region assignment receiving part 610 receives the operator's assignment of the tomographic thickness, and the main body control part 60 turns the turning arm 30 according to the assigned tomographic thickness.

As described above, in the medical X-ray photography apparatus 1, the position, the shape, and the tomographic thickness of the cutting plane can properly be set according to the purpose of the diagnostic imaging.

The change of the pseudo intraoral radiography region CA in FIG. 11B, which is performed by bringing or distancing the X-ray detector 21 close to or away from the photography target region, will supplementally be described below.

The pseudo intraoral radiography region CA in FIG. 15 includes the four teeth in which the planar cutting plane A1 and the curved cutting plane A2 are set, and the region irradiated with the X-ray cone beam BX1 enlarges when the moving mechanism 200 displaces the turning arm 30 and the photographic mechanism 3 in the −y-direction to bring the X-ray detector 21 to the pseudo intraoral radiography region CA. The enlarged region irradiated with the X-ray cone beam BX1 can be used as a new pseudo intraoral radiography region CAL.

It is assumed that a new planar cutting plane A1L and curved cutting plane A2L are set to the pseudo intraoral radiography region CAL. For example, the pseudo intraoral radiography can be performed by the setting of the turning center of the turning shaft moving control in which the turning center of the turning arm 30 is set to the central portion viewed in the Z-direction of the planar cutting plane AA or the central portion viewed in the Z-direction of the curved cutting plane A2L.

In order that the region irradiated with the X-ray cone beam BX1 is reduced to a new pseudo intraoral radiography region CAS, the moving mechanism 200 displaces the turning arm 30 and the photographic mechanism 3 in the +y-direction to distance the X-ray detector 21 away from the pseudo intraoral radiography region CA.

<Movement of Turning Arm in X-Ray Photography>

The movement of the turning arm until the end of the X-ray photography from the beginning will be described below with reference to FIGS. 16 to 19. In the X-ray photography in FIGS. 16 to 19, assuming that the photographic region CA is set to several teeth including the anterior tooth of the upper jaw in the whole jaw, the pseudo intraoral radiography is performed. However, the movement of the turning arm is not limited to the pseudo intraoral radiography, but can be applied to the panoramic photography and the CT photography.

Figure 16:
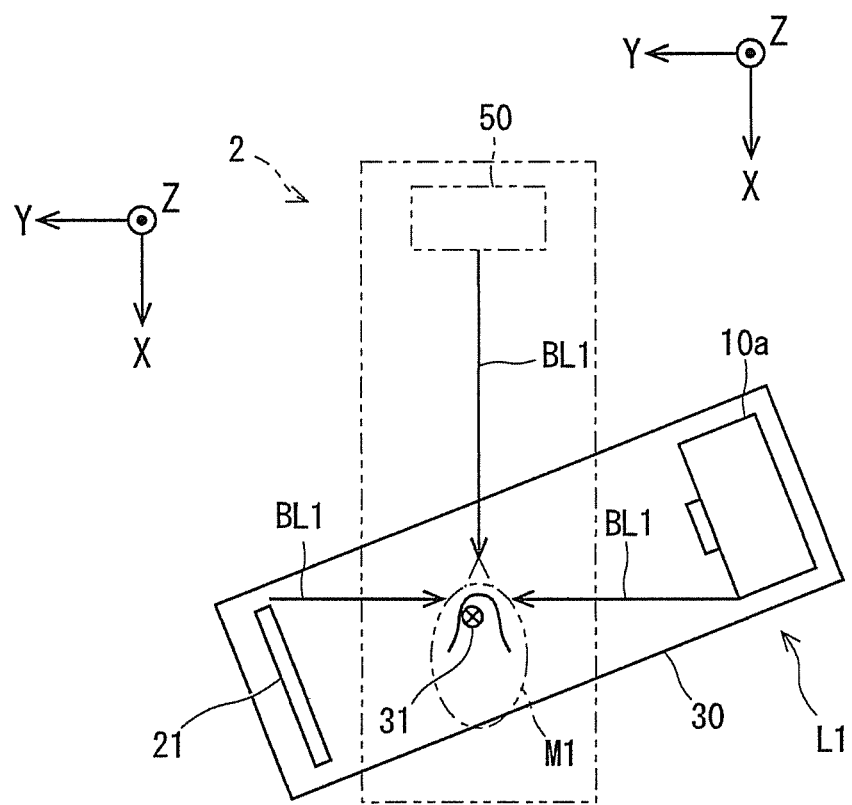
FIG. 16 is a schematic plan view illustrating a first phase of X-ray photography.
Figure 18:
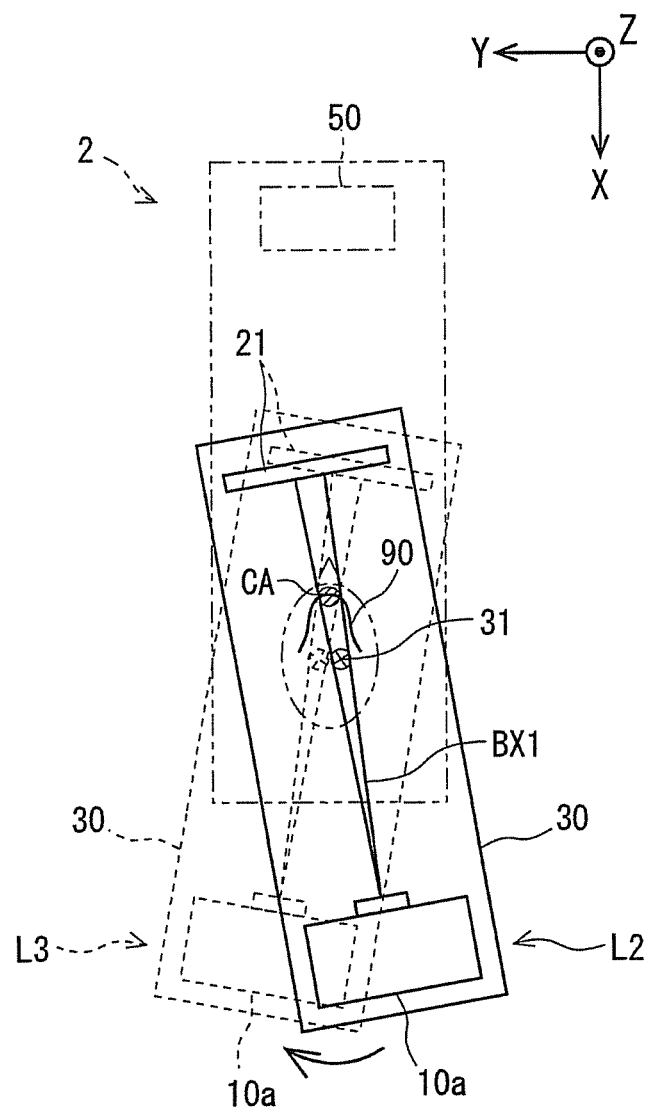
FIG. 18 is a schematic plan view illustrating a third phase of the X-ray photography.
Figure 19:
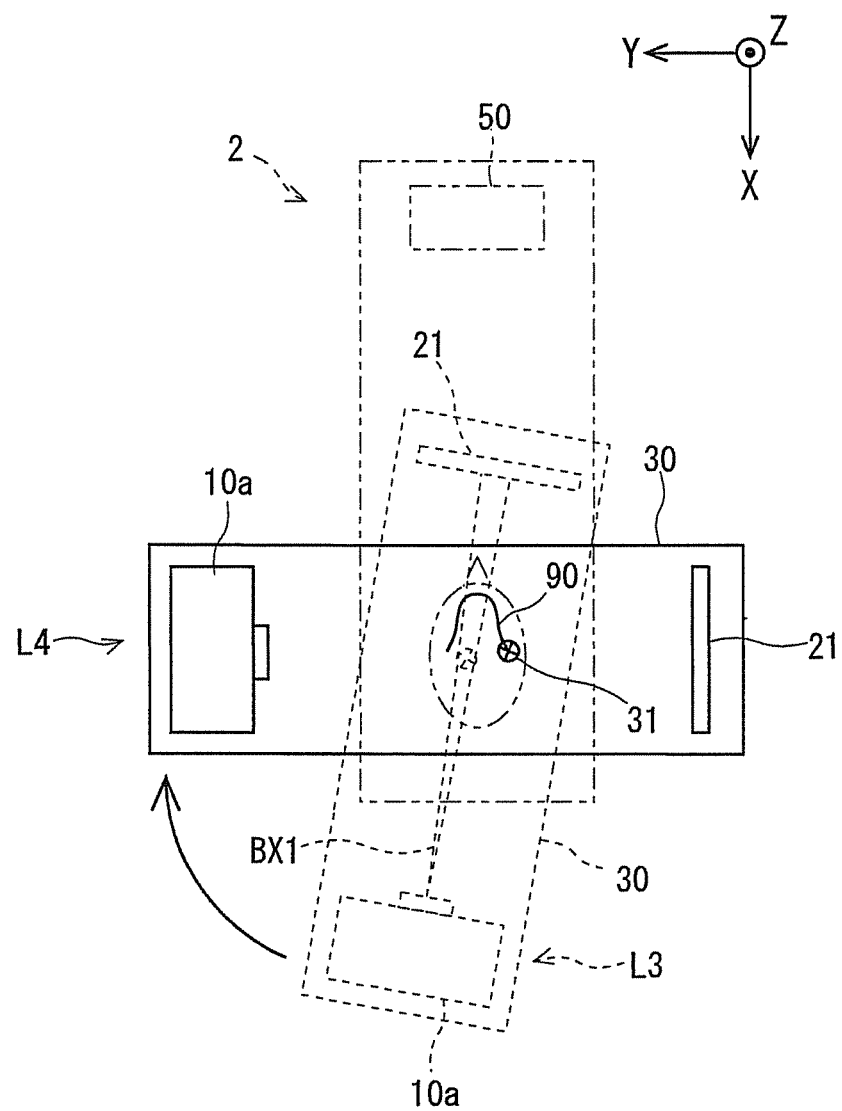
FIG. 19 is a schematic plan view illustrating a fourth phase of the X-ray photography.

In the medical X-ray photography apparatus 1, the X-ray photography is divided into a phase (a first phase) in which the subject M1 is introduced to the main body 2 of the medical X-ray photography apparatus 1, a phase (a second phase) in which the turning arm 30 is moved from an initial position L1 in FIG. 16 to a photography starting position L2 in FIG. 17 in order to perform the X-ray photography, a phase (a third phase) in which the turning arm 30 is moved from the photography starting position L2 to a photography ending position L3 in FIG. 18 in order to irradiate the subject M1 with the X-ray, a phase (a fourth phase) in which the turning arm 30 is moved to a retractable position L4 in FIG. 19 for allowing the patient to leave, and a phase (a fifth phase) in which the turning arm 30 is returned from the retractable position L4 to the initial position L1.

FIG. 16 is a schematic plan view illustrating the first phase of the X-ray photography. As illustrated in FIG. 16, in the first phase, the turning arm 30 is disposed in the initial position L1 in order to introduce the subject M1 to the main body 2. In the first phase, the turning arm 30 is usually located in the initial position in which the turning arm 30 does not become the obstacle when the patient is introduced to the X-ray photography apparatus.

In the initial position L1, a surrounding of a tooth root end of the anterior tooth is irradiated with visible light beams BL1 emitted from visible light emitting parts, which are provided in the X-ray generator 10a, the X-ray detector 21, and the pillar 50, whereby the patient is positioned in the X-ray photography apparatus. If the turning arm 30 is not located in the initial position L1, the operator operates the operation display parts 61 and 62 or the operation part 82 to move the turning arm 30 to the initial position L1.

FIG. 17 is a schematic plan view illustrating the second phase of the X-ray photography. As illustrated in FIG. 17, in the second phase, the turning arm 30 moves to the photography starting position L2, in which the photography is started, in order to irradiate the set photographic region CA with the X-ray beam BX1. As described above, the main body control part 60 receives the movement starting signal output from the signal output switch 71, whereby the turning arm 30 moves to the photography starting position L2.

In the example in FIG. 17, the photography starting position L2 is the position (an irradiation starting position) in which the irradiation of the photographic region CA with the X-ray beam BX1 is started. Alternatively, the photography starting position L2 may be set to the position located behind the irradiation starting position in the turning direction.

In the case that the scaling of the pseudo intraoral radiography region CA is performed by bringing or distancing the X-ray detector 21 close to or away from the photography target region as illustrated in FIG. 11B, the photography starting position L2 is the position obtained by moving the X-ray generator 10a and X-ray detector 21 constituting the photographic mechanism 3 in the −y-direction or the +y-direction with respect to the pseudo intraoral radiography region CA from the position in FIG. 17. In the case that the pseudo intraoral radiography region is enlarged, the photography starting position L2 is the position obtained by moving the photographic mechanism 3 in the −y-direction. In the case that the pseudo intraoral radiography region is reduced, the photography starting position L2 is the position obtained by moving the photographic mechanism 3 in the +y-direction.

FIG. 18 is a schematic plan view illustrating the third phase of the X-ray photography. As illustrated in FIG. 18, in the third phase, the turning arm 30 moves from the photography starting position L2 to the photography ending position L3. As described above, the operator operates the signal output switch 71 to output the photography starting signal to the main body control part 60, thereby moving the turning arm 30. The movement of the turning arm 30 is performed by the setting of the turning center of the turning shaft moving control.

In the example in FIG. 18, the photography ending position L3 is the position (an irradiation ending position) in which the irradiation of the photographic region CA with the X-ray beam BX1 is ended. Alternatively, the photography ending position L3 may be set to the position located slightly ahead of the irradiation ending position in the turning direction.

FIG. 19 is a schematic plan view illustrating the fourth phase of the X-ray photography. As illustrated in FIG. 19, in the fourth phase, the turning arm 30 moves from the photography ending position L3 to the retractable position L4 for allowing the subject M1 leave the main body 2. As described above, the turning arm 30 is automatically moved after a predetermined time since the turning arm 30 has moved to the photography ending position L3. The operator may operate the signal output switch 71 to move the turning arm 30 to the retractable position LA.

In the example in FIG. 19, the retractable position L4 is the position in which the turning arm 30 is parallel with the X-axis direction. The retractable position L4 is illustrated by way of example, and the retractable position L4 may be set to another position. After the subject M1 exits the X-ray photography apparatus, the turning arm 30 returns from the retractable position L4 to the initial position L1 (see FIG. 16) (the fifth phase). The operator operates the signal output switch 71 to output the return signal to the main body control part 60, thereby moving the turning arm 30.

Figure 20:
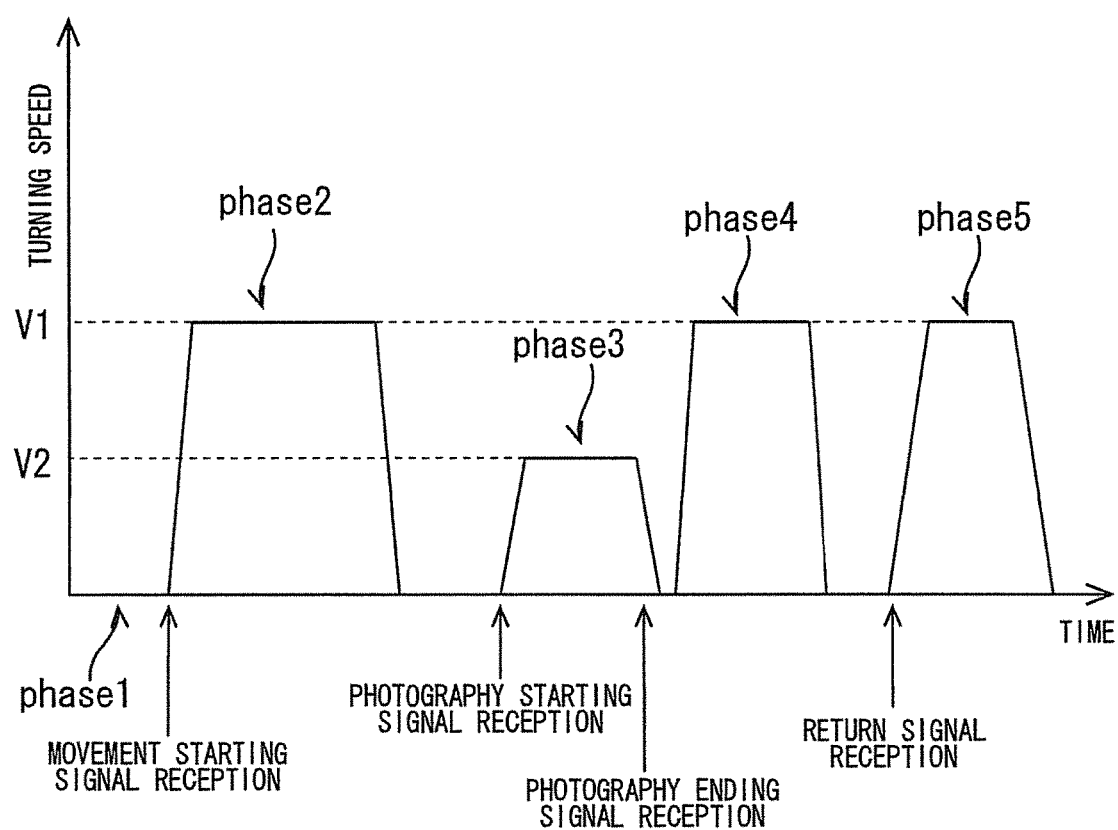
FIG. 20 is a chart illustrating a change in turning speed of a turning arm during the X-ray photography.

FIG. 20 is a view illustrating a change in turning speed of the turning arm 30 during the X-ray photography. In FIG. 20, the horizontal axis indicates time, and the vertical axis indicates a turning speed (=a rotation speed of the turning shaft 31). A phase 1 to a phase 5 in FIG. 20 correspond to the first phase to the fifth phase, respectively.

In the preferred embodiment, as illustrated in FIG. 20, a turning speed (a first turning speed V1) of the turning arm 30 in the second phase, the fourth phase, and the fifth phase (that is, the phases in which the turning arm 30 moves from the initial position L1 to the photography starting position L2, from the photography ending position L3 to the retractable position L4, and from the retractable position L4 to the initial position L1) is faster than a turning speed (s second turning speed V2) of the turning arm 30 in the third phase (that is, the phase in which the turning arm 30 moves from the photography starting position L2 to the photography ending position L3). The turning arm 30 can precisely be moved during the X-ray photography in which the subject M1 is irradiated with the X-ray beam BX1 to collect the frame data, and the turning arm 30 can rapidly be moved in other situations. Accordingly, the X-ray photography can be performed with high efficiency while the good X-ray projection image is obtained.

In the example in FIG. 20, the turning arm 30 is unified at the turning speed V1 in the second phase, the fourth phase, and the fifth phase. However, the turning speeds V1 of the second phase, the fourth phase, and the fifth phase are not necessarily be equal to one another. However, desirably the turning speeds V1 of the second phase, the fourth phase, and the fifth phase are faster than the turning speed V2.

The setting examples of the photography starting position L2 and the photography ending position L3 in the case that the opening 17 is changed to change the pseudo intraoral radiography region CA by driving the beam forming mechanism 13 in response to the deformation of the photographic region selection line 313a as illustrated in FIG. 11B will be described with reference to FIG. 21.

At this point, it is assumed that the photography starting position L2 and the photography ending position L3 of the turning arm 30 in FIG. 18 are set in order to perform the pseudo intraoral radiography of the photographic region selection line 313uc prior to the deformation operation in FIG. 11B.

Figure 21:
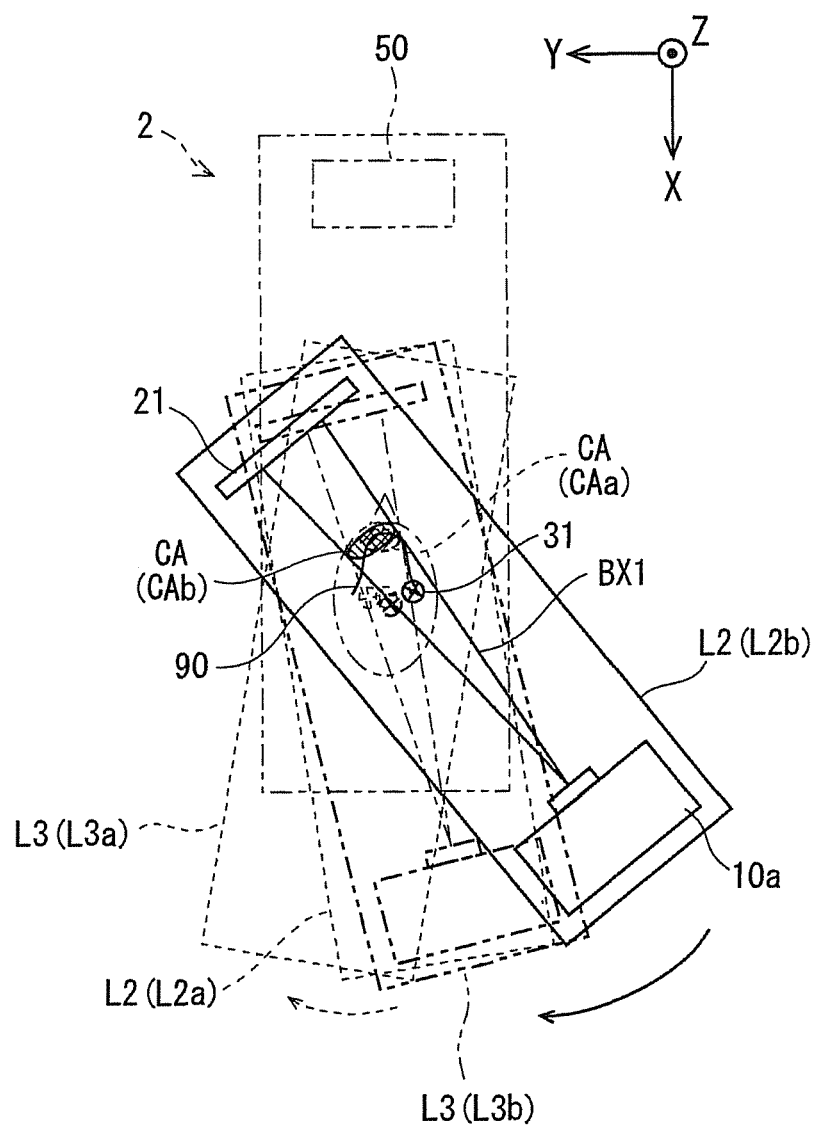
FIG. 21 is a schematic plan view illustrating a situation of the X-ray photography.

In FIG. 21, the photographic region CA that is the photographing target with the photographic region selection line 313uc prior to the deformation operation in FIG. 11B is indicated by a photographic region CAa, the photography starting position L2 in photographing the photographic region CAa of the turning arm 30 is indicated by a position L2a, and the photography ending position L3 is indicated by a position L3a. That is, the position L2a is the photography starting position L2 in FIG. 18, and the position L3a is the photography ending position L3 in FIG. 18.

As illustrated in FIG. 11B, it can be configured such that, in the case that the photographic region selection line 313uc is subjected to the deformation operation so as to become a photographic region selection line 313ucm, the photography starting position L2 and the photography ending position L3 can also be adjusted according to the changed photographic region CA.

In FIG. 21, the photographic region CA that is the photographing target corresponding to the post-deformation operation photographic region selection line 313ucm in FIG. 11B is indicated by a photographic region CAb, the photography starting position L2 in photographing the photographic region CAb of the turning arm 30 is indicated by a position L2b, and the photography ending position L3 is indicated by a position L3b.

In the example of the deformation operation in FIG. 11B, because the frame 313uc has a component enlarged toward the left side of the dental arch, the photography starting position L2b is displaced counterclockwise compared with the position L2a as illustrated in FIG. 21. The photography ending position L3b may be adjusted so as to be displaced counterclockwise compared with the position L3a as illustrated in FIG. 21.

As described above with reference to FIG. 11B, in the case where the pre-deformation operation template in FIG. 11B, specifically the pre-deformation operation photographic region selection line 313uc is subjected to the deformation operation such as the change in size, and the shape of the opening 17 of the beam forming mechanism 13 is changed according to the deformation operation, at least the X-ray photography starting position L2 can be adjusted.

In the case that the frame 313uc has a component enlarged toward the right side of the dental arch, the photography starting position L2b may be adjusted so as to be displaced clockwise compared with the position L2a. In this case, the photography ending position L3b may also be adjusted so as to be displaced clockwise compared with the position L3a.

2. Modifications

Although the preferred embodiment is described above, the present invention is not limited to the above preferred embodiment, but various modifications can be made.

For example, in the preferred embodiment, the signal output switch 71 is operated to output the photography starting signal, the turning arm 30 moves to the photography starting position L2, and the signal output switch 71 is operated to output the photography starting signal, thereby performing the X-ray photography. Alternatively, after the turning arm 30 moves to the photography starting position L2, the X-ray photography may be performed without any operation. In this case, only by performing the operation to output the movement starting signal, the turning arm 30 moves automatically to the photography starting position L2, the turning arm 30 moves automatically toward the photography ending position L3, and the X-ray irradiation is automatically started. Therefore, the operation work of the operator can be simplified during the X-ray photography.

Figure 22:
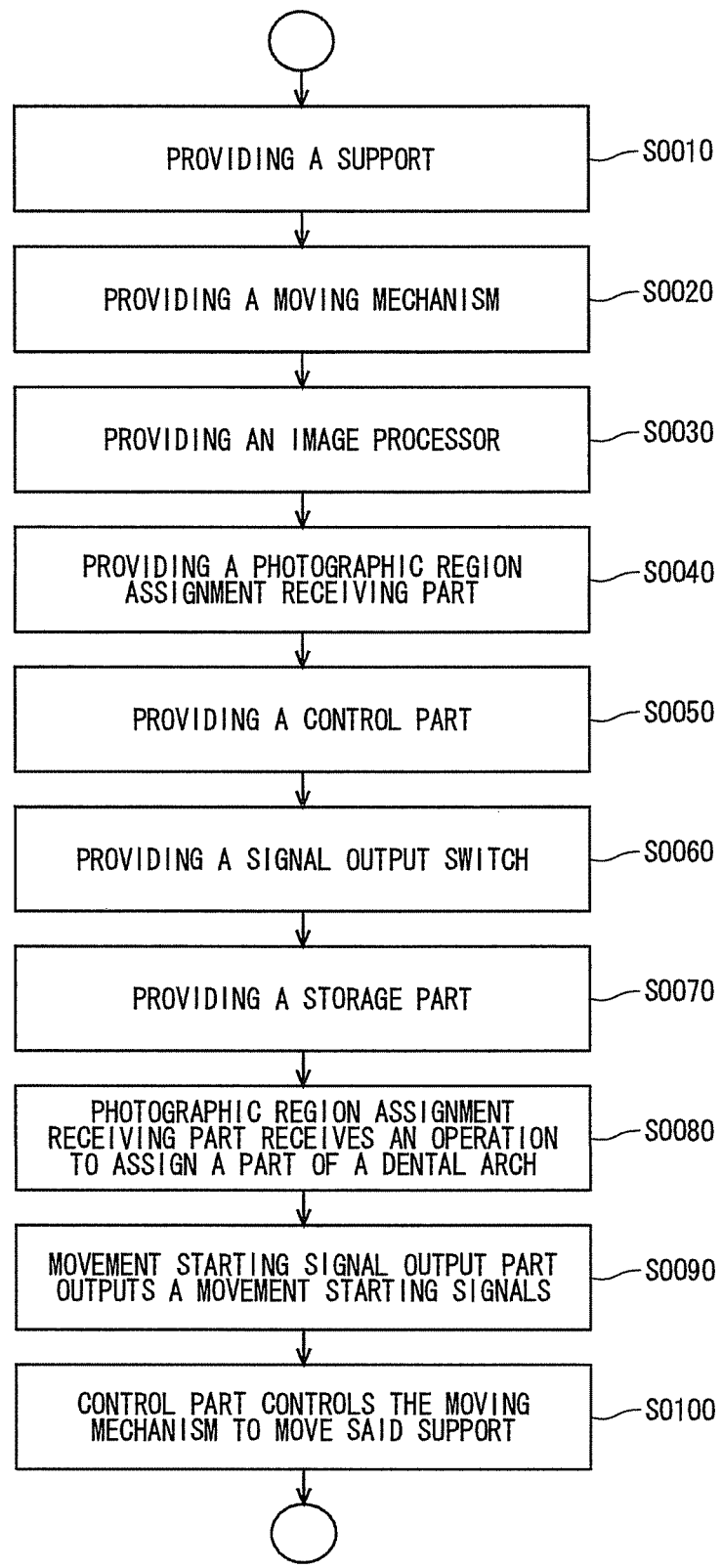
FIG. 22 shows an example of a process of the medical X-ray photography apparatus.

FIG. 22 shows an example of a process of a medical X-ray photography apparatus 1 which can be applied to the above mentioned embodiment. The process includes the following steps S0010 to S0070 for providing a medical X-ray photography apparatus. The order of the steps can be changed.

In Step S0010, a support 30, an X-ray generator 10a and an X-ray detector 21 are provided in a condition that the support 30 supports the X-ray generator 10a and the X-ray detector 21 while the X-ray generator 10a and the X-ray detector 21 are opposed to each other with a subject M1 interposed therebetween in X-ray photography, the X-ray generator 10a emits an X-ray beam, and the X-ray detector 21 outputs an electric signal according to an intensity of a detected X-ray.

In Step S0020, a moving mechanism 200 is provided to include a turning part 201 and a moving part 202 and the turning part 201 turns the support 30 about a turning shaft. The moving part 202 moves the support 30 along a two-dimensional plane orthogonal to an axial direction of the turning shaft.

In Step S0030, an image processor 801 is provided to generate an X-ray image by processing X-ray image data detected by the X-ray detector 21.

In Step S0040, a photographic region assignment receiving part 610 is provided.

In Step S0050, a control part 60 is provided.

In Step S0060, a signal output switch 71 is provided to include a movement starting signal output part 711.

In Step S0070, a storage part is provided to store a photographing condition including a condition for a movement of the support as a predetermined condition for example a photography starting position, a photography ending position and so on.

Further, the process includes the following steps S0080 to S0100 for assignment receiving and controlling.

In Step S0080, the photographic region assignment receiving part 610 receives an operation to assign a part of a dental arch 90 as a pseudo intraoral radiography region CA.

In Step S0090, the movement starting signal output part 711 outputs a movement starting signal to the control part 60.

In Step S0100, the control part 60 controls the moving mechanism 200 to move said support 30 based on the movement starting signal to a photography starting position L2 according to the photographing condition stored in the storage part corresponding to the pseudo intraoral radiography region CA set by the photographic region assignment receiving part 610.

While the invention has been shown and described in detail, the foregoing description is in all aspects illustrative and not restrictive. It is therefore understood that numerous modifications and variations can be devised without departing from the scope of the invention.

What is claimed is:

1. A medical X-ray photography apparatus comprising:
an X-ray generator emitting an X-ray beam;
an X-ray detector outputting an electric signal as an X-ray image data according to an intensity of a detected X-ray;
a support that supports the X-ray generator and the X-ray detector opposed to each other with a subject interposed therebetween;
an actuator which turns said support about a turning shaft, and moves said support along a two-dimensional plane orthogonal to an axial direction of said turning shaft;
a shield configured for regulating the X-ray beam emitted from the X-ray generator, the shield comprising a plurality of plates, configured to form an adjustable opening;
an interface including a display, said interface receives an operation to assign a radiography region, said radiography region including a row of teeth along a dental arch as a pseudo intraoral radiography region, said radiography region including a plurality of predetermined sub-regions, each sub-region including a cutting plane, a location of which a tomographic image is reconstructed;
wherein
the display is configured to display the plurality of predetermined sub-regions, such that a plurality of frame lines are superimposed on a panoramic image or an illustration of a panoramic image of a jaw, each of said frame lines representing each of said sub-regions being set based on a photographing region of a multiple photographing method of conventional intraoral radiography, said multiple photographing method being 10-film method or 14-film method,
the medical X-ray photography apparatus is configured to receive an input of the operation to assign the radiography region by an operation to select one of said plurality of frame lines,
the shield forms an irradiating X-ray cone beam via the adjustable opening to said pseudo intraoral radiography region having a width to irradiate each of said sub-regions of said pseudo intraoral radiography region, according to any selectively modified sub-regions indicated by the user input via the interface,
the actuator is configured to move the support to execute a radiography of said pseudo intraoral radiography region by way of tomography of an extra-oral radiography in a tomosynthesis as a pseudo intraoral radiography in which the X-ray generator and the X-ray detector rotate around a head of the subject in a state that a turning center is set in said pseudo intraoral radiography region so that said X-ray cone beam intersects each cutting plane, and
the actuator moves said support from a predetermined radiography starting position to a predetermined radiography ending position during said pseudo intraoral radiography and changes each of the radiography starting position and the radiography ending position according to a change of a position of the pseudo intraoral radiography region among the plurality of sub-regions.

2. The medical X-ray photography apparatus according to claim 1, further comprising a signal output switch, said signal output switch including a photography starting signal output part that outputs a photography starting signal to said actuator based on reception of a predetermined operation, and when receiving said photography starting signal, said actuator starts turning of said support from said radiography starting position to said radiography ending position corresponding to said pseudo intraoral radiography region.

3. The medical X-ray photography apparatus according to claim 2, wherein the signal output switch outputs a movement starting signal based on reception of a predetermined operation, and the actuator is controlled to move said support to said radiography starting position when receiving said movement starting signal.

4. The medical X-ray photography apparatus according to claim 1, further comprising a multiple-photographing method selector that receives selection of a specific photographing method from a plurality of different multiple-photographing methods, said interface displaying said plurality of frame lines corresponding to the multiple-photographing method selected by said multiple-photographing method selector while arranging said frame line on said panoramic image or said illustration of the panoramic image.

5. The medical X-ray photography apparatus according to claim 1, a change in size of said frame line being possible by an operation using said interface, and when the size of said frame line is changed, said radiography starting position is adjusted while changing said adjustable opening formed by the shield according to the change in size of the frame line.

6. The medical X-ray photography apparatus according to claim 2, a first turning speed at which said actuator moves said support to said radiography starting position being faster than a second turning speed at which said actuator turns said support from said radiography starting position to said radiography ending position.

7. The medical X-ray photography apparatus according to claim 1, said interface receiving an assignment of at least one of a length along said dental arch and a vertical height orthogonal to the dental arch with respect to said pseudo intraoral radiography region.

8. The medical X-ray photography apparatus according to claim 1, further comprising a storage that stores the radiography starting position and the radiography ending position as a radiography condition corresponding to said pseudo intraoral radiography region, said radiography condition being retrievable from the storage when input of the pseudo intraoral radiography region is received.

9. A medical X-ray photography apparatus comprising:
an X-ray generator emitting an X-ray beam;
an X-ray detector outputting an electric signal as an X-ray image data according to an intensity of a detected X-ray;
a support that supports the X-ray generator and the X-ray detector opposed to each other with a subject interposed therebetween;
an actuator which turns said support about a turning shaft, and moves said support along a two-dimensional plane orthogonal to an axial direction of said turning shaft;
a shield configured for regulating the X-ray beam emitted from the X-ray generator, the shield comprising a plurality of plates, configured to form an adjustable opening;
an interface including a display which receives an operation to assign a radiography region, said radiography region including a row of teeth along a dental arch as a pseudo intraoral radiography region, said radiography region including a plurality of predetermined sub-regions, each sub-region including a cutting plane, a location of which a tomographic image is reconstructed;
wherein
the display is configured to display the plurality of predetermined sub-regions, each of said sub-regions having an individual form and size different from other ones of the sub-regions, such that a plurality of frame lines are superimposed on a panoramic image or an illustration of a panoramic image of a jaw, each of said frame lines representing each of said sub-regions being set based on a photographing region of a multiple photographing method of conventional intraoral radiography, said multiple photographing method being 10-film method or 14-film method,
the X-ray medical photography apparatus is configured to receive an input of the operation to assign the radiography region by an operation to select one of said plurality of frame lines,
the shield forms an irradiating X-ray cone beam via the adjustable opening to said pseudo intraoral radiography region regulated so as to irradiate a whole of a selected sub-region, according to the user input via the interface,
the actuator is configured to move the support to execute a radiography of said pseudo intraoral radiography region by way of tomography of an extra-oral radiography in a tomosynthesis as a pseudo intraoral radiography in which the X-ray generator and the X-ray detector rotate around a head of the subject in a state that a turning center is set in said pseudo intraoral radiography region so that said X-ray cone beam intersects each cutting plane, and
the actuator moves said support from a predetermined radiography starting position to a predetermined radiography ending position during said pseudo intraoral radiography and changes each of the radiography starting position and the radiography ending position according to a change of a position of the pseudo intraoral radiography region among the plurality of sub-regions.

10. The medical X-ray photography apparatus according to claim 9, further comprising a multiple-photographing method selector that receives selection of a specific photographing method from a plurality of different multiple photographing methods, said interface displaying said plurality of frame lines corresponding to the multiple-photographing method selected by said multiple-photographing method selector while arranging said frame line on said panoramic image or said illustration of the panoramic image.

11. The medical X-ray photography apparatus according to claim 9, said interface receiving an assignment of at least one of a length along said dental arch and a vertical height orthogonal to the dental arch with respect to said pseudo intraoral radiography region.

12. The medical X-ray photography apparatus according to claim 9, further comprising a storage that stores the radiography starting position and the radiography ending position as a radiography condition corresponding to said pseudo intraoral radiography region, said radiography condition being retrievable from the storage when input of the pseudo intraoral radiography region is received.

\* \* \* \* \*